United States Patent
Lu et al.

(10) Patent No.: US 8,500,620 B2
(45) Date of Patent: *Aug. 6, 2013

(54) VENTRICULAR ASSIST DEVICE

(75) Inventors: Pong-Jeu Lu, Tainan (TW); Pao-Yen Lin, Tainan (TW); Jiin-Huey Chern Lin, Winnetka, IL (US); Chien-Ping Ju, Kansas City, MO (US)

(73) Assignee: National Cheng Kung University, Tainan (TW)

( * ) Notice: Subject to any disclaimer, the term of this patent is extended or adjusted under 35 U.S.C. 154(b) by 938 days.

This patent is subject to a terminal disclaimer.

(21) Appl. No.: 12/181,128

(22) Filed: Jul. 28, 2008

(65) Prior Publication Data

US 2008/0306329 A1    Dec. 11, 2008

Related U.S. Application Data

(63) Continuation of application No. PCT/US2007/001906, filed on Jan. 25, 2007.

(60) Provisional application No. 60/763,143, filed on Jan. 30, 2006.

(51) Int. Cl.
*A61M 1/12* (2006.01)
(52) U.S. Cl.
USPC .............................................................. 600/16
(58) Field of Classification Search
USPC ............... 600/16; 623/1.1, 1.21, 1.3, 1.31, 623/1.38, 1.39; 128/912
See application file for complete search history.

(56) References Cited

U.S. PATENT DOCUMENTS

| | | | |
|---|---|---|---|
| 4,503,568 A * | 3/1985 | Madras | 623/1.3 |
| 4,573,997 A | 3/1986 | Wisman et al. | |
| 4,690,134 A | 9/1987 | Snyders | |
| 4,731,073 A | 3/1988 | Robinson | |
| 4,888,011 A | 12/1989 | Kung et al. | |
| 5,332,403 A * | 7/1994 | Kolff | 623/3.21 |
| 5,910,124 A | 6/1999 | Rubin | |
| 5,928,132 A | 7/1999 | Leschinsky | |
| 6,146,325 A | 11/2000 | Lewis et al. | |
| 6,540,666 B1 | 4/2003 | Chekanov | |
| 6,582,463 B1 * | 6/2003 | Mowry et al. | 623/1.35 |

(Continued)

FOREIGN PATENT DOCUMENTS

| | | |
|---|---|---|
| JP | 10-248923 A | 9/1998 |
| WO | 2007089500 | 8/2007 |
| WO | 2008138956 | 11/2008 |
| WO | 2009088916 | 7/2009 |

OTHER PUBLICATIONS

Hoffman, Allan S., "Blood-Biomaterial Interactions; An Overview," American Chemical Society, pp. 3-8 (1982).*

(Continued)

*Primary Examiner* — Carl H Layno
*Assistant Examiner* — Paula J Stice
(74) *Attorney, Agent, or Firm* — Rosenberg, Klein & Lee

(57) ABSTRACT

A manifold for accessing blood from a human blood vessel is disclosed which comprises a first and a second pathway intersecting with each other at an angle, the first pathway being configured to be completed embedded in the human blood vessel with the second pathway leading toward outside of the human blood vessel wherein the manifold is substantially retained by the human blood vessel alone.

17 Claims, 18 Drawing Sheets

U.S. PATENT DOCUMENTS

| | | | |
|---|---|---|---|
| 6,605,053 B1 * | 8/2003 | Kamm et al. | 604/8 |
| 6,821,294 B2 * | 11/2004 | Nunez et al. | 623/1.3 |
| 7,066,874 B2 | 6/2006 | Riebman et al. | |
| 7,217,236 B2 | 5/2007 | Calderon et al. | |
| 7,258,679 B2 | 8/2007 | Moore et al. | |
| 7,269,460 B2 | 9/2007 | Chinchoy | |
| 7,291,105 B2 | 11/2007 | Lau et al. | |
| 7,367,959 B2 | 5/2008 | Nardi | |
| 2001/0041929 A1 * | 11/2001 | Oepen | 623/1.15 |
| 2007/0005127 A1 | 1/2007 | Boekstegers et al. | |
| 2007/0260108 A1 | 11/2007 | Criscione | |
| 2008/0300447 A1 | 12/2008 | Lu et al. | |
| 2009/0306755 A1 * | 12/2009 | Dickinson et al. | 623/1.3 |

OTHER PUBLICATIONS

First Use of the TandemHeart Percutaneous Left Ventricular Assist Device article, 2 pages.

* cited by examiner

VENTRICULAR ASSIST DEVICE

CROSS REFERENCE

This application is a national stage of PCT/US2007/001906 filed on 25 Jan. 2007, which claims priority from U.S. Patent Application No. 60/763,143 filed on 30 Jan. 2006.

FIELD OF THE INVENTION

The present invention is related to ventricular assist devices (VAD), and in particular to a manifold for accessing blood from a human blood vessel.

BACKGROUND OF THE INVENTION

In U.S. heart failure is a major public health problem whose management consumes about 1% of the national health care resources. Approximately 3 to 4 million Americans were afflicted by heart failure, with 400,000 new cases being diagnosed each year. Heart transplantation has been the most effective therapy as compared to other medical treatments. Nevertheless, cardiac transplantation remained limited by the complications of long-term immunosuppressive therapy, allograft coronary artery diseases, and most critically, the serious shortage of donors. The annual number, of donor heart remains much constantly around 2,000. However, the patients who are qualified to receive donor heart are estimated to be 16,500 annually.

Mechanical circulation support (MCS) systems, both total artificial heart (TAH) and ventricular assist device (VAD) have been intensively studied, hoping to replace the role of heart transplantation for end-stage heart failure patients. Left ventricular assist device (LVAD) is versatile in providing heart failure patients. With therapies including bridge to transplantation, bridge to recovery and alternative to transplantation. The large-scale REMATCH (Randomized Evaluation of Mechanical Assistance for the Treatment of Congestive Heart Failure) trial, which involved 19 medical centers and 129 end-stage heart failure patients, indicates that, for patients treated by LVAD or pharmacologic therapy, one-year survival rate of the LVAD group doubles that of the pharmacologic group. Moreover, LVAD group enjoys much better quality of life during the period of support. It has been an accepted fact in cardiology society that a total implantable long-term (3-5 years) mechanical circulation support device, in particular the LVAD, will solve the current dilemma of donor shortage for the heart failure patients.

LVADs have been developed in recent years into a new medical modality that is expected to either work as a short-term bridge-to-transplantation support or replace in a long-term manner as an alternative of heart transplantation. Continuous flow LVADs are smaller but thrombogenic, and the non-pulsatile circulation support may induce many complications in micro-circulation in end organs when used chronically. Pulsatile LVADs are more physiologically compatible, but the bulkiness and larger energy consumption prevents them from being widely adopted.

An ideal mechanical circulation support (MCS) design should possess, but not limited to, the following characteristics: it 1) provides sufficient and adaptive cardiac support according to various physiological conditions or therapeutic requirements, 2) avoids blood trauma and device-induced complications, 3) requires simple implantation procedure and post-operational care, and 4) guarantees safety operation and allows emergent salvage including necessary device maintenance/repair or replacement. To date, none of the leading-edge LVAD products can meet all these requirements.

SUMMARY OF THE INVENTION

The embodiments provide a ventricular assist device (VAD), which avoids the major drawbacks associated with the traditional VADs.

The embodiments also provide a dual-pulsation bi-ventricular assist device (DPbi-VAD), which comprises a dual-pulsation mechanism enforcing co-pulsation and counter-pulsation circulation support.

The embodiments also provide a method for treating a patient suffering a cardiac disease by using the dual-pulsation bi-ventricular assist device of the present invention.

The embodiments achieve the DPbi-VAD by two approaches. First approach, a sac is used to directly compress the heart, especially to only compress the left and right ventricles. Second approach, a manifold and a blood pump is used to the flood flow out the aorta and flow in the aorta in sequence. Therefore, by properly control the timing of compression and pumping, the heart failure is improved.

Moreover, the two approaches could improve the heat failure independently. In other word, the embodiments provide a ventricular assist device that is based on a sac for wrapping around a heart, and the embodiments also provide another ventricular assist device that is based on a manifold for accessing blood from a human blood vessel and a blood pump for pumping flood from the human blood vessel through the manifold.

The embodiments further provide some specific designs on the sac the manifold and the blood pump.

One specific embodiment is a ventricular assist device (VAD). The VAD has a sac for wrapping around a heart and blood outlet made to an aorta. Herein, the sac has one or more inflatable chambers, for compressing the heart when the chambers being inflated, and the blood outlet is the sole opening in the human blood path in the vicinity of heart. Moreover, during a systolic phase the inflatable chambers inflate while blood flows out of the aorta through the blood outlet, and during a diastolic phase the inflatable chambers deflate while blood flows into the aorta through the blood outlet.

The specific embodiment has some modification about the sac. For example, the sac could comprise a substantially rigid outer shell with a shape substantially confirm the shape of the heart the ventricular assist device is applied to. For example, the sac could comprise an elastic membrane hermetically attached to the inner surface of the outer shell, wherein the space between the outer shell and the elastic membrane forms the inflatable chamber. For example, the inflatable chambers could be placed substantially on ventricular free walls of the heart. For example, each of the inflatable chambers could have at east one opening for de-airing thereof. For example, each of the inflatable chambers could be controllably connected to a driver, wherein the inflation of the inflatable chambers is individually adjustable. For example, the inflatable chambers could be inflated by a medium selected from a group consisting of liquid and gas.

The specific embodiment has some modification about the blood outlet. For example, the blood outlet could comprise a manifold having a first and a second pathway intersecting with each other at an angle, the first pathway being completed embedded in the aorta with the second pathway leading toward outside of the aorta. Herein, the manifold could have at least one of the following variations: (1) the manifold could be valveless. (2) The manifold could be made of a biocompatible material selected from the group consisting of metal and elastic polymer. (3) The wall thickness of the manifold could gradually decreases toward a first and a second end of the first pathway. (4) The wall of the manifold could be perforated along tire first pathway. (5) The wall of the manifold could be textured along the first pathway. (6) Both the first and second pathways of the manifold could have a circular cross-section.

The specific embodiment has some modification about the blood outlet. For example, the blood outlet could comprise a blood pump having a first compartment connected to the blood outlet, wherein the volume of the first compartment increases during the systolic phase and decreases during a diastolic phase. Herein, the blood pump could further comprises a second compartment and an outer shell, the outer shell enclosing both the first and second compartments, the volume of the outer shell remaining substantially constant during both the systolic and diastolic phases, the first and second compartment being separated by an elastic membrane, the volume of the second compartment decreasing during the systolic phase, and the volume of the second compartment increasing during the diastolic phase. Herein, the blood pump could have at least one of the following variations: (1) the second compartment could be substantially filled with a medium, the medium being driven out of and into the second compartment during the systolic and diastolic phase, respectively. Further, the medium is selected from the group consisting of liquid and gas. (2) Both the first and second compartments have at least one de-airing opening.

As discussed above, the two approaches of the presented DPbi-VAD could be used to improve the heart failure separately. Therefore, many embodiments could be a subset of the previous specific embodiment.

The construction and method of operation of the invention, however, together with additional objectives and advantages thereof will be best understood from the following description of specific embodiments when read in connection with the accompanying drawings.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting, embodiments illustrated in the drawings, wherein like reference numbers (if they occur in more than one view) designate the same elements. The invention may be better understood by reference to one or more of these drawings in combination with the description presented herein.

FIG. 4b is a schematic cross-sectional view showing the stent-like manifold in FIG. 4a.

FIG. 5b is a schematic cross-sectional view showing the tissue-engineered manifold in FIG. 5a.

DETAILED DESCRIPTION OF THE INVENTION

Dual-Pulsation Design Concept

Figure 1A:
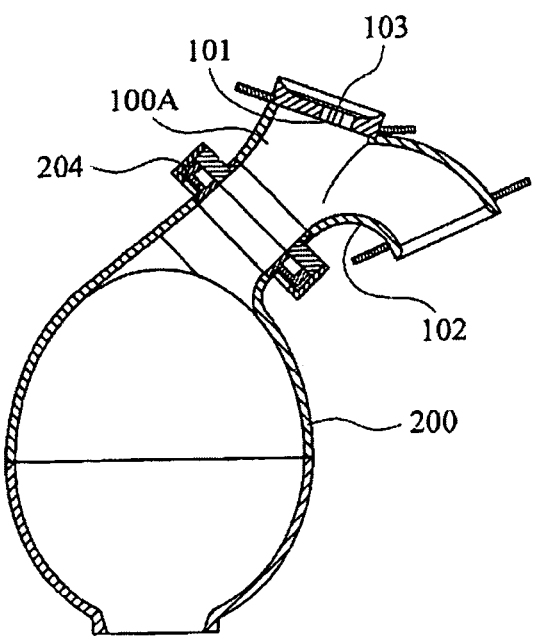
FIG. 1a is a schematic cross-sectional view showing a manifold and blood pump assembly of the present invention, to be implanted at ascending aorta.

The design of an integrated co- and counter-pulsation bi-ventricular assist device proposes in the following several novel design features which will improve the aforementioned inadequacies existing in the contemporary LVAD designs. Basically, the adoption of the pulsatile: pumping approach is based on two; major considerations including: 1) the implanted device functions compatibly with the human physiology; and 2) the long-term patency is guaranteed which assures both operational safety and quality of life for the patients. Pulsatile circulation assist is much physiologically compatible, and in order not to induce long-term complications, in particular, in end organ micro-circulation and neurohormonal regulation, it is logically more sensible to consider pulsatile circulatory support. Owing to the fact that pulsatile devices are non-obligatory, it is safer for patients to survive by their own native heart function when unexpected pump malfunction occurs. In addition, for pulsatile LVADs, less device-induced blood trauma and hence a reduced or no reliance on anticoagulant therapy warrants, to a significant extent, the patient's post-operational life quality.

The contemporary switching to continuous flow design is thought, in the present inventors' opinion, to be a trade of exchanging mechanical challenges to physiological complications. Normally, a proper approach to solve the mechanical design difficulties pertaining to the LVADs should attempt to seek solution methods in reducing the size and energy consumption requirements, rather than exchanging them with non-physiological pumping which may very possibly induce hew, unknown and refractory long-term complications to occur.

Counter-pulsation has proven to be useful for reducing-systolic afterload and increasing diastolic coronary perfusion for diseased hearts. Co-pulsation cardiac compression, however, may assist in the cardiac contraction by a direct, synchronous epicardial compression of the right and left Ventricles. These two pumping characteristics can only be implemented by using pulsatile devices. For either counter-pulsation or co-pulsation circulatory support, the trigger of mechanical actuation that imparts energy into the blood circulation requires a precise phase control relative to the natural heart rhythm. To date, devices employing individual counter-pulsation or co-pulsation principle have been proposed and designed separately. A synergistic use of counter-pulsation and co-pulsation circulation supports in one single device forms the basis of the present bi-VAD design principle.

Imagine a mechanical device that can assist the blood circulation by a coordinated co- and counter-pulsation during heart systole, with the upstream ventricular contractility being increased while downstream vascular afterload being reduced; the resultant effectiveness in cardiac output enhancement would be much greatly elevated as compared to those only support circulation via either upstream or downstream assistance. In the diastolic mode, counter-pulsation pumping enforced from within the aorta may assist coronary perfusion similarly as did by the conventional, well-proven intra-aortic balloon pump (IABP) devices. Moreover, during diastole another co-pulsation function of the device provides a mechanical containment effect that prevents the diseased heart from further abnormal dilation. This simultaneous use of co- and counter-pulsations in the improvement of cardiac hemodynamics and myocardial contraction and relaxation is termed herein, and will be referred to, as dual-pulsation cardiac assist, and the hardware that facilitates this special circulation support modality is given a name as "Dual-Pulsation Bi-Ventricular Assist Device," abbreviated DPbi-VAD.

The significance and impact of dual-pulsation cardiac assist to the pulsatile LVAD design is at least triple-fold. First, it reduces the energy requirement of the conventional pulsatile driver design. The retrograde energy originally wasted in extracting working fluids (air or silicon oil) back from the pumping unit into the compliance chamber is retrieved and converted as the energy for systolic compression support. This push-and-pull type operation exerted from both up and downstream ends of the native ventricles can cut considerably down the driver energy expenditure, resulting in a unique feature that cannot be enjoyed by any contemporary pulsatile devices. Second, the need for extra space for accommodating compliance chamber is eliminated. Compliance chamber, as redesigned in the present DPbi-VAD, turns an originally purely useless volume storage pouch into a functioning systolic compression support unit. Hence, compliance chamber is no longer an indispensable liability to the pulsatile devices. The thoracic cavity spared for a natural heart to function is now dynamically shared by the compliance chamber (or the sac). Third, the inflow/outflow grafts are no longer the bypass flow passages that must be equipped for LVAD to function. Notice that almost all the past and contemporary ventricular assist devices need to use synthetic grafts, typically those fabricated from polyethylene terephthalate (Dacron) or expanded polytetrafluoroethylene (ePTFE), as duct passages; for implementing blood drainage from ventricle/atrium and for facilitating blood re-entry, after mechanical pressurization, back into the vasculature bed. Clinically graft cannulation and anastomosis, which must be conducted with cardiopulmonary bypass (CPB) support, occupies a large portion of the surgical time accompanying with substantial perioperational bleeding and thrombotic risks. It was observed statistically that many post-operational complications, such as thrombus formation, graft kinking, bleeding, and pannus overgrowth are associated with these inflow/outflow grafts. The present single-port inflow/outflow design for facilitating counter-pulsation circulation support revolutionizes the traditional graft anastomosis. Virtually no conventional synthetic grafts are required for the present DPbi-VAD and the anastomosis can be carried out by a beating heart surgery. A specially designed semi-rigid manifold is introduced to result in a much shorter and more streamlined passage for blood flow to come in and out of the blood pump of DPbi-VAD. These aforementioned new characteristic features reverse the general impression that pulsatile LVAD implantation is more complex and difficult due to the necessity of implanting more and bulky components in a congested thoracic space.

It was found clinically that nearly 30% LVAD recipients died from right heart failure. To date, pre-operational markers that can define the suitability of LVAD implantation are yet satisfactorily developed. Often, LVAD recipients would require additional RVAD implantation to assist to the induced right heart failure. Otherwise, the pulmonary pressure will be elevated and the filling of the LVAD and hence the delivered cardiac output enhancement will be impaired due to inadequate right ventricular contractility. The presently proposed DPbi-VAD solves this problem completely by employing a direct cardiac compression on both right and left ventricles. With the co-pulsation operation of the sac, both pulmonary and systemic circulations are assisted simultaneously. During this bi-ventricular support, homogeneous pressurization enforced around the free wall of the heart prevents the septum movement which has long been an observed complication for all the LVAD implantations using left ventricular apical coring for blood bypass. This bi-ventricular circulation support forms another important and unique feature for the present device. When implanted with DPbi-VAD, it is believed that the risk associated with the traditional LVAD implantation will be significantly reduced owing to a balanced bi-ventricular circulation support.

The present innovative DPbi-VAD design also simplifies the implantation procedure and greatly reduces the surgical risks. Beating-heart surgery can be employed in the present DPbi-VAD implantation. For the DPbi-VAD implantation, apical coring is no longer required for unloading the left ventricle as well as for filling the blood pump. The in-series blood flow drainage and re-entry is presently facilitated by a single-port manifold accessed, for example, from the descending aorta, making possible the intact heart VAD implantation that demands no CPB procedure.

In summary, DPbi-VAD allows a pairing dual-pulsation synergism be accomplished to remedy the traditional drawbacks associated with the pulsatile devices. The salutary IABP-generated counter-pulsation is retained; however, the traditional IABP shortcoming of inadequate cardiac output enhancement due to occlusive, intravascular balloon deployment is improved by using a non-occlusive, para-aortic blood pump anastomosed end-to-side to the arterial vessel. Direct cardiac compression offered by the sac additionally enhances the cardiac contractility. The conversion of traditional compliance chamber into bi-ventricular sac not only resolves the excessive space requirement problem, but also proactively strengthens the ventricular contractility by using otherwise wasted retrograde energy. Balanced/right and left heart support is also achieved naturally to avoid the LVAD-induced right heart failure. This sac can further therapeutically contain the dilated heart in the diastole mode. Graft cannulation is also revolutionized in the present DPbi-VAD design. The mono-port inflow/outflow access to blood flow simplifies the surgical procedure and reduces the mortality and morbidity associated with the graft-induced complications. With the incorporation of dual-pulsation assist in cardiac support, it is anticipated that the original high-energy and excessive surgical space requirements, as well as difficult-to-implant characteristics of the pulsatile devices will be improved significantly. In treating failing hearts, all the therapeutic hemodynamic and mechanical functions, i.e. systolic unloading, diastolic augmentation, cardiac output enhancement and passive mechanical containment are synergistically retained. Most importantly, DPbi-VAD is able to provide all these mechanical therapeutic remedies while leaving the diseased heart intact. Those clinical and surgical advantages will inspire a new though and protocol development for treating heart failure patients with advance MCS engagement under lower mortality and morbidity rates. Bridge-to-recovery will be set as a primary objective for heart failure treatment, leaving bridge-to-transplantation and destination therapy the next prioritized considerations.

DPbi-VAD System Description

The DPbi-VAD system could have the following six modules: 1) manifold, 2) blood pump, 3) intra- and/or extra-corporeal driver systems, 4) physiological controller, 5) sac, and 6) energy/information transfer system. Each module is shown respectively in the following figures, with the explanations of the design features and function characteristics being elucidated to illustrate its role played with and specifications required by the whole system.

a. Manifold

Manifold constitutes a unified inflow/outflow port for DPbi-VAD to connect to the aorta. This para-aortic manifold Can be a valved or valveless two-way duct. Each option has its own design goals to achieve and the choice of which type manifold is more suitable depends on the clinical indications, surgical complexity, and the judgment the physician is having in mind prior to the implantation. FIGS. 1 and 2 show respectively a representative manifold layout intended to be implanted to the ascending or descending aorta. Basically the manifold is configured by merging together two stream directions. Flow passages are kept as streamlined as possible to reduce momentum loss as well as turbulence generation during pulsatile actuation of the blood pump.

Figures 1B, 1C:
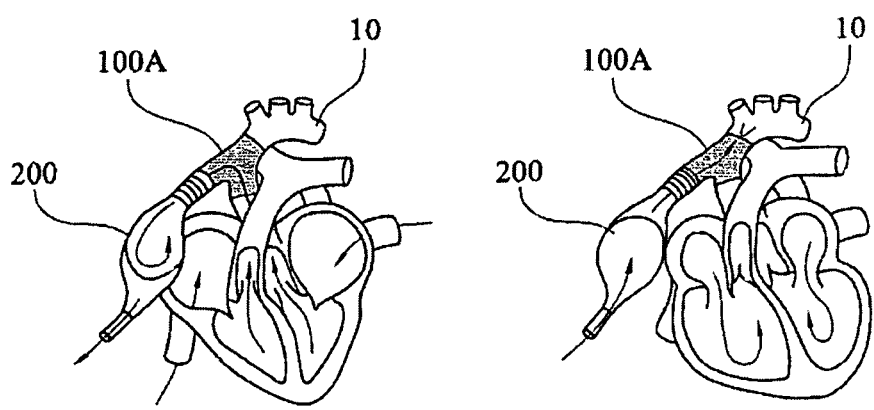
FIG. 1b is a schematic view showing the manifold and blood pump assembly in FIG. 1a implanted at ascending aorta during pump operation at systolic phase.
FIG. 1c is a schematic view showing the manifold and blood pump assembly in FIG. 1a implanted at ascending aorta during pump operation at diastolic phase.

As shown in FIG. 1a, the ascending manifold 100A, connected to a blood pump 200 with a quick connector 204, has a tangential distal outflow tract 101 for ejecting blood stream into the aorta 10 (FIG. 1c) and a curved proximal duct 102 for blood pump filling (FIG. 1b). This design aims to minimize the total pressure loss and turbulence generation, which occurs frequently in the high-speed pump ejection phase, as blood passes through the conduit duct. The distal end could be either valveless or mounted with an artificial valve 103 to regulate the blood flow direction. A jellyfish valve is used herein because of its low-cost, good hemodynamic: performance, low valve sound, and thrombo-resistance offered by a seamless integration to the conduit wall. Mechanical or porcine prosthetic: valves can also be adopted though they are more expensive. The valved manifold possesses a better pump filling efficacy and most importantly, it prevents the cerebral blood retrogression during the pump filling phase. The disadvantages, of course, are valve-induced hemolysis and thromboembolism, in addition to the transvalvular energy loss due to higher flow resistance caused by valve occlusion.

Figure 2A:
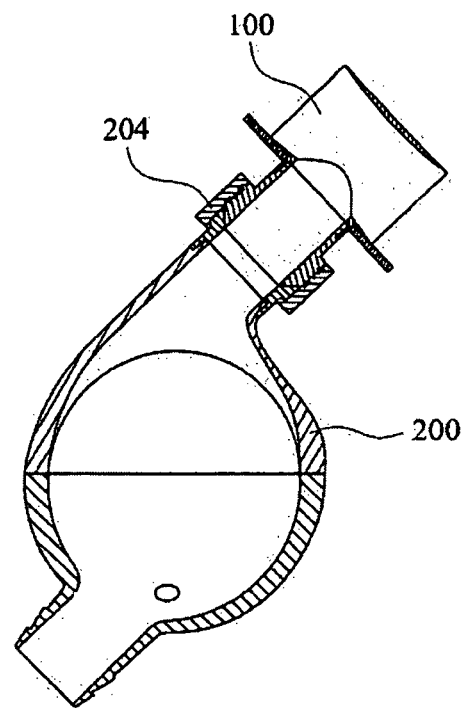
FIG. 2a is a schematic cross-sectional view showing a manifold and blood pump assembly of the present invention, to be implanted at descending aorta.

As shown in FIG. 2a, the descending manifold 100, however, is a T-shaped conduit connected to a blood pump 200 with a quick connector 204. During the systolic phase, direct cardiac compression is offered by a sac 500 with the help from an electro-hydraulic driver 300 while undergoing blood pump filling from the aorta 10 to the blood pump 200 (FIG. 2b) via the descending manifold 100. During the diastolic phase (FIG. 2c), blood in the blood pump 200 is ejected into the aorta 10 via the descending manifold 100. The intersecting angle at the junction can be varied to yield different flow resistances hence biased perfusions to the up and downstream blood circulation. Like the ascending manifold, the descending manifold can also be valved or valveless. The installation of a prosthetic valve is helpful for a more effective systolic unloading provided by the blood pump 200, because this one-way flow regulation of the descending aortic flow can avoid the volume displacement caused by the femoral circulation retrogression. Since the descending aortic placement of manifold 100 and blood pump 200 involves a longer lumen distance from the inflow/outflow port to the aortic root, the counter-pulsation actuation should take into account the phase delay due to the finite distance traveled by the imparted pressure pulse in the aorta before it reaches the aortic root. Descending manifold placement minimizes the possibility of cerebral stroke because, when blood pump 200 ejects, the device-induced clots or microembli are relatively difficult to convect upstream to the brain owing to larger traveling distance and smaller convection wave speed involved.

Descending valveless manifold is most attractive because it possesses two major clinical advantages. First, descending anastomosis can be performed with beating heart surgery. Second, artificial valve-induced complications can altogether be avoided. Since a T-junction flow passage is not physiologic, therefore, vascular maladaptation that encourages thrombus formation, intimal hyperplasia and smooth muscle cell overgrowth may occur. In order to optimize the flow and stress conditions, special designs for coping with this end-to-side anastomosis are proposed. These propositions include, but not limited to, the subsequent design alternatives: 1) compliance-matching manifold, 2) stent-like manifold and 3) tissue engineered manifold, as described in the following.

1. Compliance-Matching Manifold

Figure 3A:
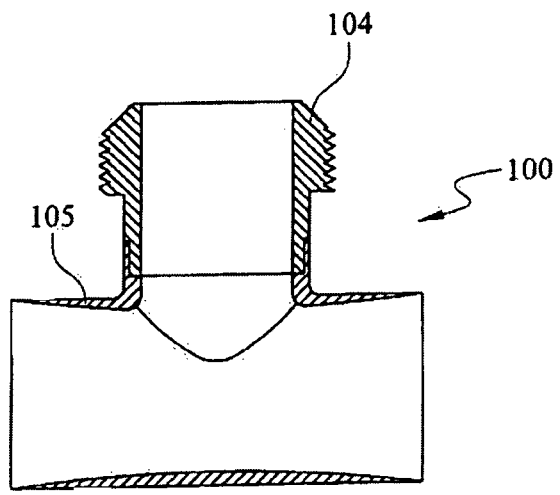
FIG. 3a is a schematic cross-sectional view showing a compliance-matching manifold of the present invention.

Compliance mismatching has known to be the main causal factor for stenosis at the anastomotic junction. The jump of compliance at the graft ends results in geometric discontinuity when subjected to blood pressure pulsation. Geometric discontinuity causes high wall shear stress gradient being generated at the graft/vessel junction and low-speed recirculation flow occurring in the immediate downstream, leading to endothelial cell erosion and diffusion-induced cell proliferation around the anastomotic site. Compliance-matching graft design aims at eliminating this compliance discontinuity phenomenon at the graft/vessel junctions. Shown in FIG. 3a is the compliance-matching manifold design principle. The graft could be fabricated by elastic polymers such as, but not limited to, polyurethane. This compliance-matching manifold 100 has a second pathway 104 for connecting to the blood pump, and a first pathway 105 being adapted to be implanted in the aorta (or to access blood from a human blood vessel). Herein, first pathway 105 and second pathway 104 intersect with each other at an angle. The first pathway 105 possesses gradually thinning wall thickness toward its two ends. Since wall compliance is inversely proportional to the product of wall thickness and Young's modulus pertaining, to the graft/vessel material, a compliance-matching graft should have a sharp-edged, or zero-thickness conduit end configuration. The graft diameter could be designed a little bit larger (0~20%) than the diameter of the inner aortic lumen. When insertion type anastomosis is applied to place the varying-wall-thickness graft embedded inside the aortic lumen, a tight fit of overlaid graft and aorta can be achieved using suturing method to result in a continuous varying compliance over the overlapped graft/vessel region.

Figure 3B:
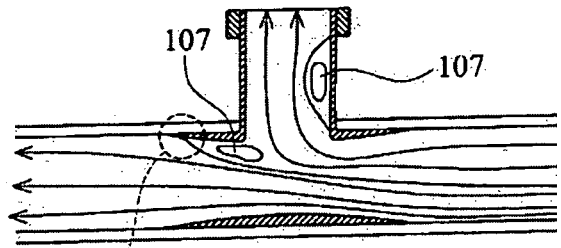
FIG. 3b is a schematic cross-sectional view showing the hemodynamic characteristics of the compliance-matching manifold in FIG. 3a during pump operation at systolic phase.
Figure 3C:
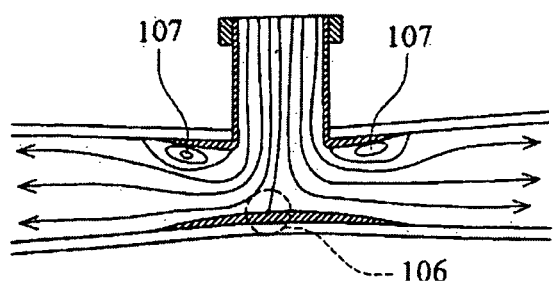
FIG. 3c is a schematic cross-sectional view showing the hemodynamic characteristics of the compliance-matching manifold in FIG. 3a during pump operation at diastolic phase.

This manifold 100 has many hemodynamic and biological advantages. The smooth and compliance-matching junction design minimizes the propensity of stenosis and intimal hyperplasia occurring around the anastomotic site. Streamlined flow pattern can be maintained as much as possible by a smooth, continuously varying composite lumen configuration. Such low-turbulence duct design is the optimum that ah end-to-side anastomosis can attain. Generally speaking, in the pump filling and ejection phases, as shown respectively in FIGS. 3b and 3c, separated flow related high-pressure stagnation zones 106 as well as low-speed recirculation regions 107 take place in the vicinity of the T-junction. These non-physiological flow characteristics are the major factors that cause blood cell trauma and pathologic vascular adaptations. However, for the present manifold design and anastomosis, the lining non-biological graft baffles the natural vessel from being afflicted by these abnormal and mixed high-shear and low-speed flow characteristics. It is worth noticing that this baffling effect protects the surgical wound from high pressurization, hence greatly reducing the possibility of peri- and post-operational bleeding complications. Aside from the end regions where low-compliance dominates, the central manifold is actually a hard-walled graft. This hard wall is more advantageous for facilitating counter-pulsation coronary blood perfusion. Diastolic augmentation is found sensitive to the vessel wall elasticity. The insertion type anastomosis, in fact, replaces a portion of the natural vessel by a hard-walled graft. As blood pump ejects the highest stagnation flow region is directly contained and resisted by the hard-walled manifold. The overall wall compliance is therefore decreased which is welcome as considered by the facilitation of diastolic augmentation.

2. Stent-Like Manifold

Figure 4A:
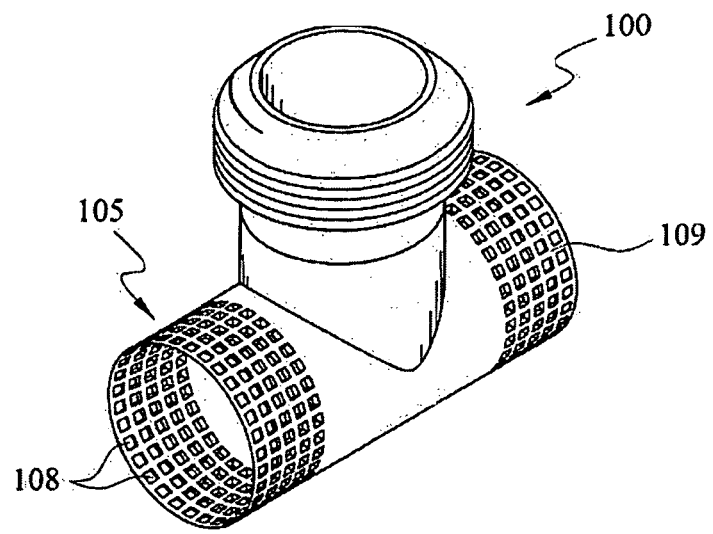
FIG. 4a is a schematic perspective view showing a stent-like manifold of the present invention.
Figure 4B:
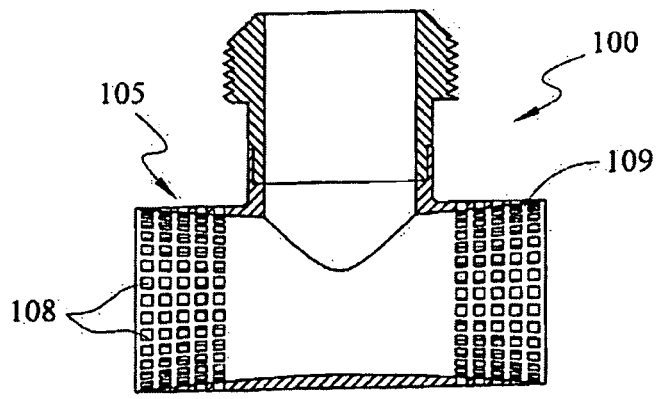

Another embodiment of the manifold is achieved by way of stenting the manifold graft. FIGS. 4a and 4b show a schematic of this design concept. The manifold 100 is constructed using biocompatible metal materials such as stainless steel, titanium or titanium alloys. On the aorta-embedded duct portion (the first pathway 105), holes or perforations 108 of various shapes and porosity ratios can be distributed to form perforated walls 109, allowing endothelium cell migration in the same manner as observed in the stented blood vessel. The stent porosity can be varying, with higher porosity (lower modulus) regions located around the graft/vessel junctions. Although compliance-matching is relatively difficult to achieve presently as compared to the aforementioned compliance-matching polymer graft design, the endothelialization, after certain period after implantation, will sandwich and embed the stent-like manifold inside the aortic lumen, resulting in a neon composite, vessel of higher rigidity in the central region and a softer and smoother geometric/compliance transition around the ends. For arteries of larger diameter (> 6~9 mm), re-stennosis is rarely found clinically due to the higher flow velocity effect. Thrombo-resistance is guaranteed by the neonintima layer produced by the stent characteristics of the graft structure. Lower compliance of the stented arterial portion may well enhance the diastolic augmentation as does the manifold.

3. Tissue-Engineered Manifold

Figure 5A:
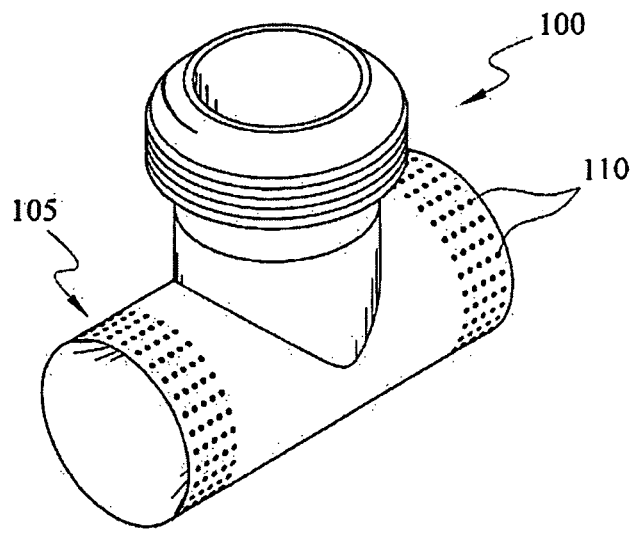
FIG. 5a is a schematic perspective view showing a tissue-engineered manifold of the present invention.
Figure 5B:
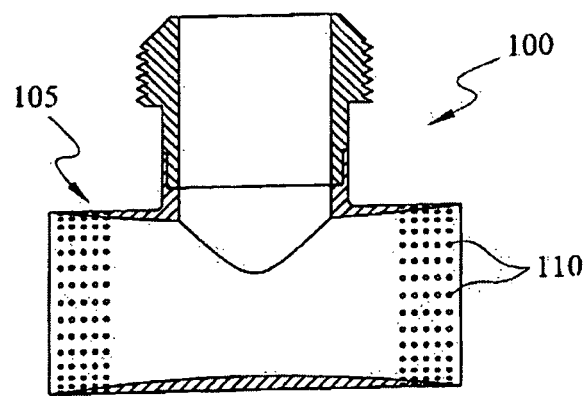

Tissue-engineered manifold is another variant of the compliance-matching graft design. The graft material used can be those elastic polymers mentioned previously. Tiny micropores or cavities 110 of small dimensions (30~300 microns) can be manufactured and distributed around certain desired inner or outer wall surface areas on the first pathway 105 of the manifold (see FIGS. 5a and 5b). These textured polymer surfaces work as the scaffold for cells in the blood stream to adhere and grow. The anchored dense thrombi will further encourage blood cell interactions to occur. A heterogeneous surface containing platelets, monocytes, macrophages, foreign-body giant cells, lymphocytes, etc. will be deposited after device implantation. Over time, a neonintima proliferated with endothelial cells will populate; over the textured area of the manifold. Preferably these tissue-engineered neonintima is located at the graft/vessel junctions. This may further enhance the junction performance in terms of better compliance-matching, smoother geometry transition, and stronger graft adherence to the artery.

b. Blood Pump

Figure 6:
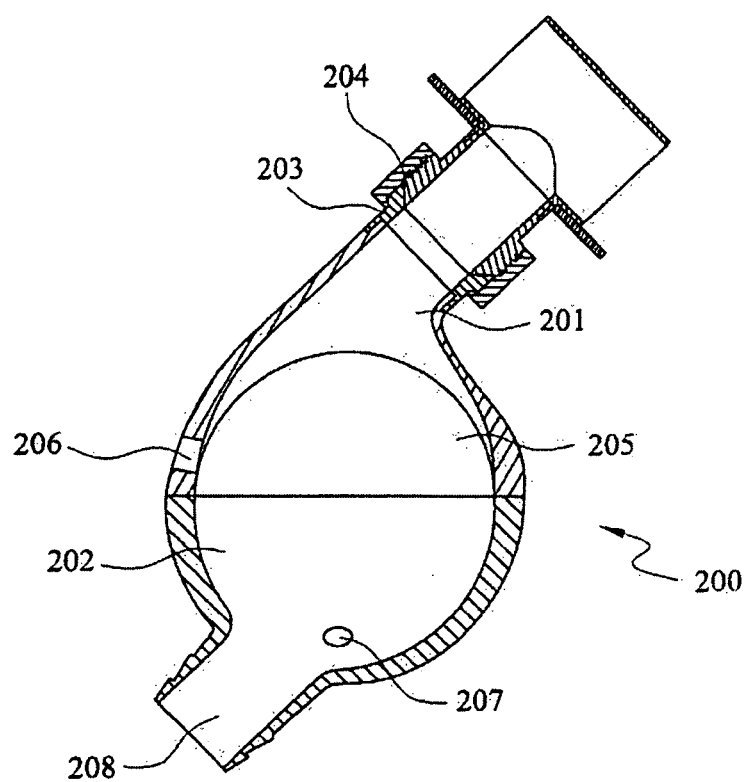
FIG. 6 is a schematic cross-sectional view of a circular-shaped blood pump of the present invention.

Blood pump works alternately as a reservoir to receive the blood volume and an ejector to propel the stored blood volume back to the artery. This blood pump 200 comprises a single-port design, with an elastic membrane 205 separating the blood in the first compartment 201 and the silicon working fluid in the second compartment 202, as illustrated in FIG. 6. Biocompatible material (e.g. polyurethane) is used to construct this blood pump. The basic form, or a circular-shaped geometry, helps flow wash-put effect be fully accomplished in the pump chamber. The inflow/outflow port 203, however, may be placed tangentially with eccentricity relative to the pump centerline to help develop flow swirl. The stroke volume of the pump can range from 30 to 100 c.c. or larger, depending on the thoracic space that is allowed and the propelling power the driver is designed to deliver.

Figure 7A:
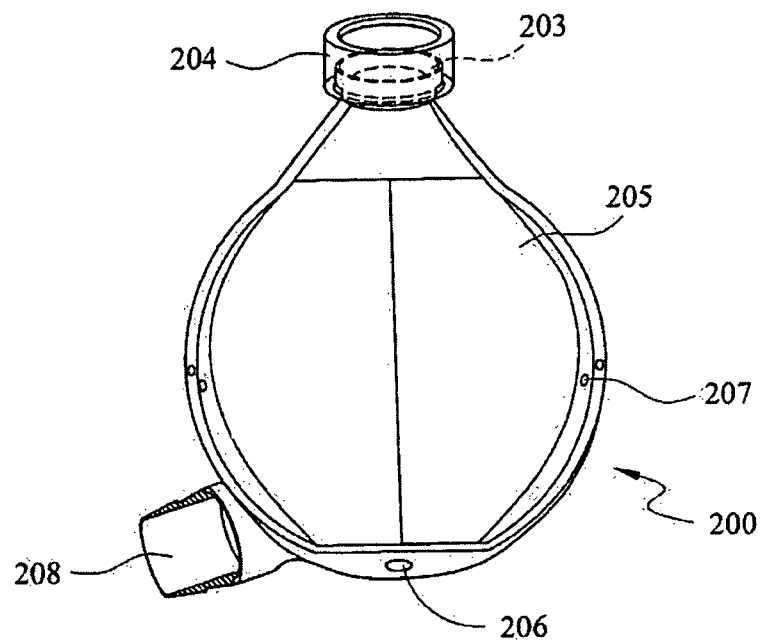
FIG. 7a is a schematic view of a body-fitted blood pump of the present invention, in which one side of the outer shell is assumed being transparent.
Figure 7B:
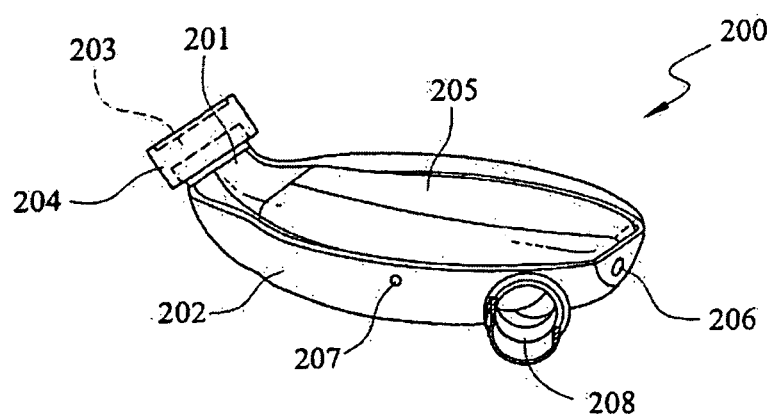
FIG. 7b is a schematic view of the body-fitted blood pump in FIG. 7a at a different angle.

FIGS. 7a and 7b show another variant of the blood pump design similar to that shown in FIG. 6, wherein like parts are designated by same numerals. The shape of this blood pump 200 looks like a flat, curved ellipsoid. Salient angles are avoided to result in a streamlined contour. The outer shell is configured by conforming its contour to the inner thoracic cage wall. This body-fitted design allows the maximum usage of the thoracic space which leads to a minimal interference with the lung. The stroke volume of the pump could range from 30 to 100 c.c. or larger.

In both circular-shaped and body-fitted pump designs blood and working fluid are separated by a elastic membrane. For circular-shaped blood pump shown in FIG. 6, the elastic membrane 205 has a zero-stress shape which is nearly identical to the pump shell configuration. The elastic membrane 205 is attached and sealed around the central inner periphery of the pump shell. For body-fitted blood pump shown in FIGS. 7a and 7b, however, the elastic membrane, or actually a sac 205 with similar but smaller shape to the outer shell, attaches to the inflow/outflow port 203 tangentially. In both designs the hard outer shell restrains the stretching of the sac, and hence prolongs the service life of the elastic membrane by limiting the elastic membrane strain well below the fatigue-related threshold. As circular-shaped pump ejects the elastic membrane 205 moves upward and barely touches the shell inner surface, leaving a small amount of blood reserve remaining in the pump. In the next pump filling phase this residual blood volume will be washed away and mixed with the newly replenished blood. As for body-fitted pump in full-volume ejection, the sac 205 is compressed fully until the opposite elastic membranes thereof may touch each other with minimal residual volume of the first compartment 201 in the sac 205 remained; and when pump fills, the sac 205 resumes its original zero-stress, wrinkle-free full shape, with the volume of the second compartment 202 diminishes, which is formed between the sac 205 and the outer shell of the blood pump 200. For partial volume ejection, however, blood stored can still be ejected completely out of the pump, though requiring several more strokes. The stasis-free characteristic of the present pump designs is attributed to the vortex-washing effect provided by the shell and elastic membrane contour in conjunction with the unsteady pulsatile flow motion.

De-airing opening is placed in the blood pump wall for air removal. The location is selected around the uppermost region where, air bubbles are collected when blood pump is implanted via left thoracotomy. For circular-shaped pump shown in FIG. 6, the de-airing opening 206 is placed in the vicinity of the elastic membrane attachment rim. For body-fitted pump, however, the de-airing opening 206 is located at the bottom of the sac where the sac attachment and fixation stub is housed, as shown in FIGS. 7a and 7b.

As shown in FIGS. 6, 7a and 7b, the upper end of the blood pump has a quick connector 204 mounted around the throat to yield a convenient quick assembly or detachment of the pump 200 to the manifold. Silicon gasket is used to enable a tight integration Of the blood pump with the manifold. At the bottom end, however, the pump shell converges into a circular duct 208 to allow connection to the driver. Similar quick connector design like that used for manifold/blood pump integration is adopted for efficient pump/driver installation. Shuttling silicon oil flowing into and out of the blood pump can be accomplished by the use of an intra- or extra-corporeal driver system. Additional de-airing opening 207 is built on the pump casing shell to aid in air removal when assembling blood pump together with the driver.

c. Intra- and Extra-Corporeal Driver Systems

1. Intra-Corporeal Driver System

The present intra-corporeal driver design adopts the hydraulic pumping principle. The designed electro-hydraulic (EH) driver consists, of two electrically-driven direct current (DC) brushless motors, one for torque generation and another for flow direction regulation, in additional to an impeller and a switching valve. The use of pressurized hydraulic fluid, or silicon oil, enables a power deployment with literally no constraints posed on the position and orientation of the actuated mechanism. The present EH driver actuates blood pump and sac asynchronously by referencing the electrocardiogram (ECG) waveform. Cannulas, through which pressurized hydraulic working fluid, runs, are used for power transmission. Quick connectors enable fast and convenient assembly/detachment and orientation adjustment of the EH driver body as connected to the blood pump and/or the sac.

For pulsatile flow pumping, the search of an isolated optimal design point is neither critical nor practical because during pump operation a loop, rather than a fixed point, shows on the pump performance map. Often; an overall high-efficiency plateau spanning a certain operational loop range should be looked for. In order to ease the implantation, more often than not, the pursuit of a miniature LVAD design demands the anatomic or space consideration a more prioritized design criterion, leaving the high operational hydraulic efficiency the next objective to achieve.

In the present DPbi-VAD driver design, the two DC brushless motors are immersed in the silicon oil bath contained in the EH driver. The heat generated comes mainly from the amateur windings and the electronic controllers. The sloshing motion of the oil flow may serve as an effective cooling mechanism for convecting and redistributing the dissipated heat to the surfaces of the whole. DPbi-VAD, including outer shells, cannulas, and elastic membranes in contacting with the circulating blood stream. Heat, hence, can be transferred locally by conduction to the tissues which surround the VAD implant or globally by convection throughput the human circulation system to the entire body. There will be literally no hot spots produced in the present electro-hydraulic design, which is an important factor for increasing the reliability of the electronics and thus for prolonging the service life of the DPbi-VAD in operation.

There are two electro-hydraulic driver designs that are presented in the following. One uses mixed-flow and the other centrifugal impeller design, depending respectively on the emphasis of either efficiency or head-rise that is stressed.

1.1 Mixed-Flow Driver

Figure 8A:
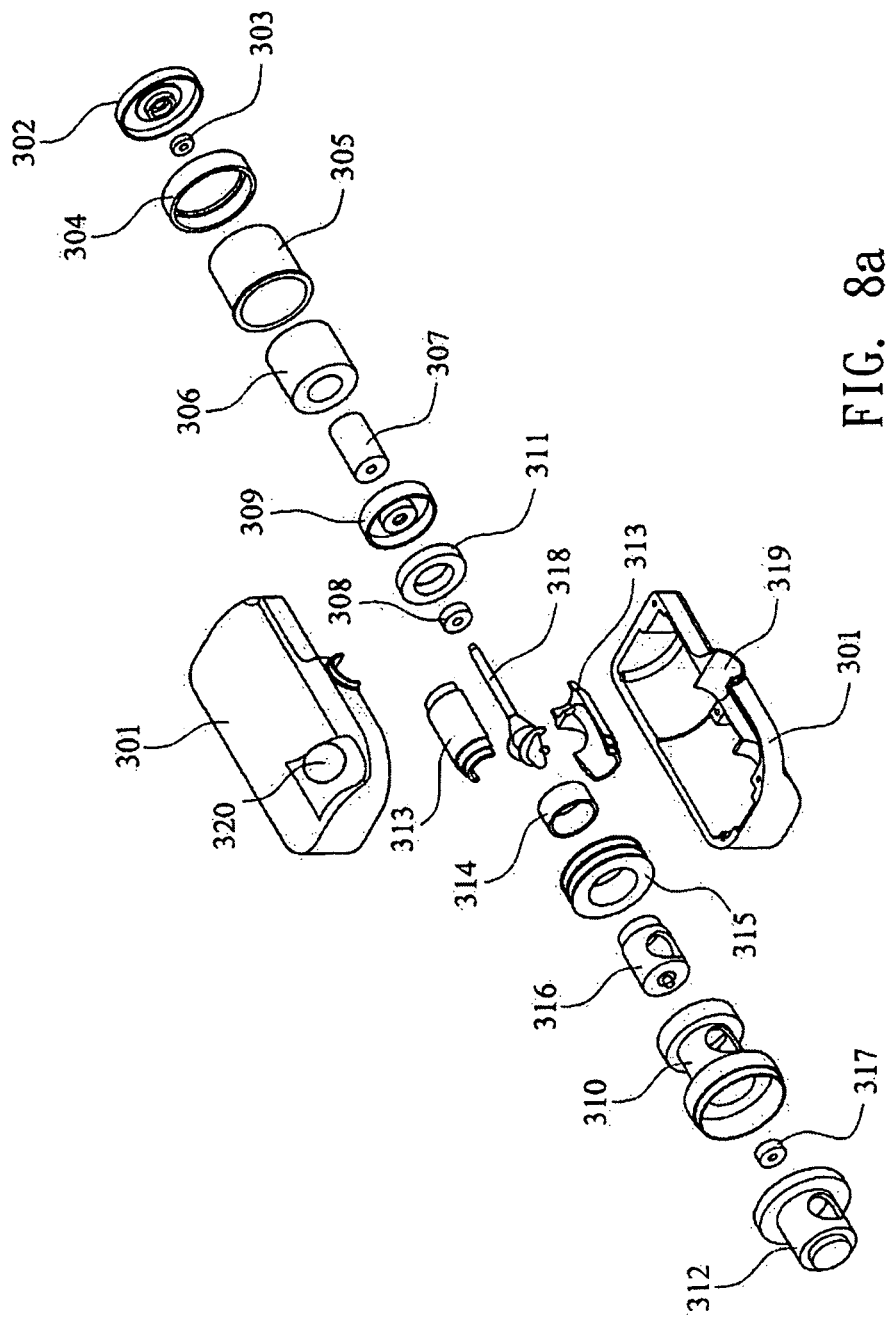
FIG. 8a is a perspective view of a mixed-flow electro-hydraulic driver used in the present invention before assembly.
Figure 8B:
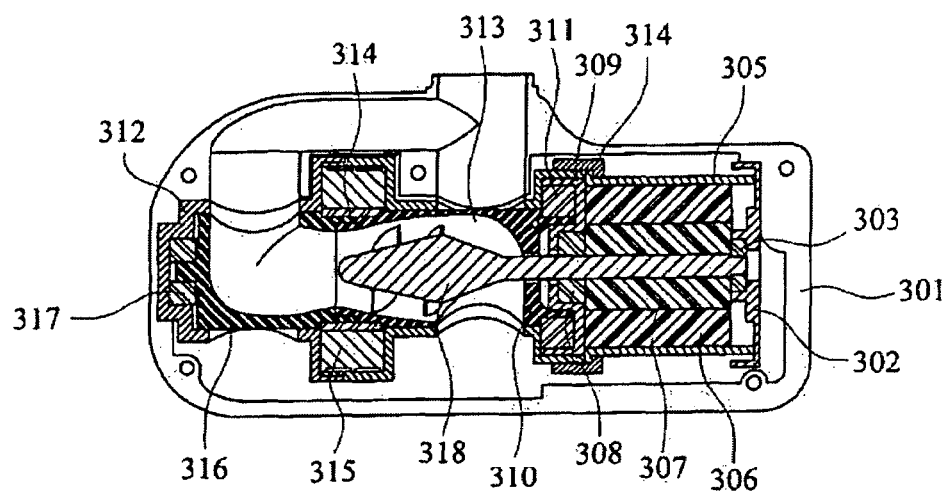
FIG. 8b is a cross-section view of the mixed-flow electro-hydraulic driver in FIG. 8a after assembly.

A mixed-flow electro-hydraulic driver constructed according to one of the preferred embodiments of the present invention is shown in FIGS. 8a and 8b, which is assembled with the flowing elements/parts:

301 Driver Casing;
302 Base Cap,
303 Bearing,
304 Lock Ring,
305 Torque Motor Casing,
306 Torque Motor Stator,
307 Torque Motor Rotor,
308 Bearing,
309 Lock Ring,
310 Switching Valve Body,
311 Bearing,
312 Switching Valve Head,
313 Switching Valve Outflow Duct,
314 Stepping Motor Rotor,
315 Stepping Motor Stator,
316 Switching Valve Inflow Duct,
317 Bearing, and
318 Mixed-flow Impeller.

The impeller 318 is housed in an inner switching valve formed by the switching valve outflow duct 313 and the switching valve inflow duct 316 which are non-rotatably engaged with each other, and the inner switching valve is rotatably disposed in the stationary casing formed by the switching valve body 310 and the switching valve head 312.

Figures 2B, 2C:
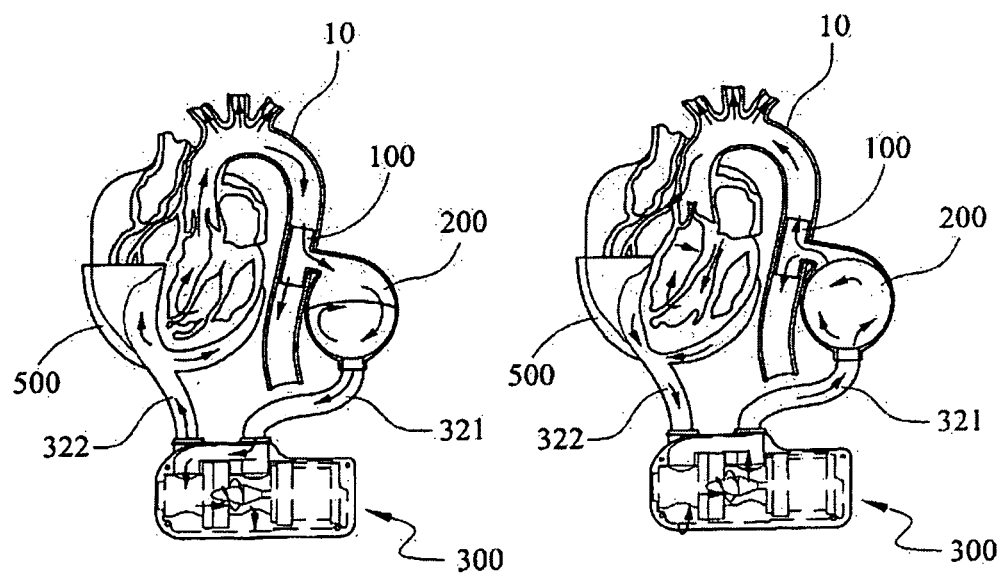
FIG. 2b is a schematic cross-sectional view showing the manifold and blood pump assembly in FIG. 2a implanted at descending aorta during pump operation at systolic phase.
FIG. 2c is a schematic cross-sectional view showing the manifold and blood pump assembly in FIG. 2a implanted at descending aorta during pump operation at diastolic phase.
Figure 9A:
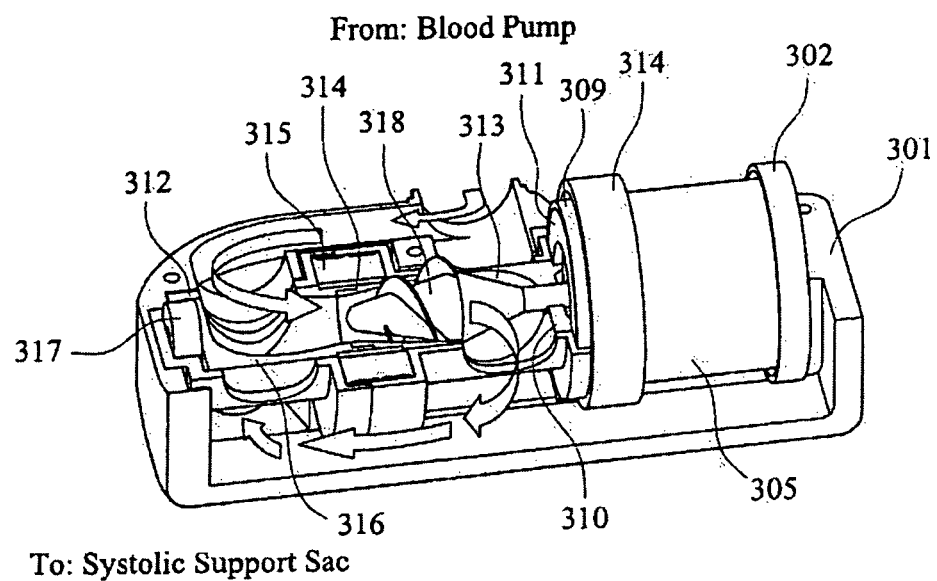
FIG. 9a shows a flow passage in the mixed-flow electro-hydraulic driver in FIGS. 8a and, 8b, wherein the flow passage is from bipod pump to sac.
Figure 9B:
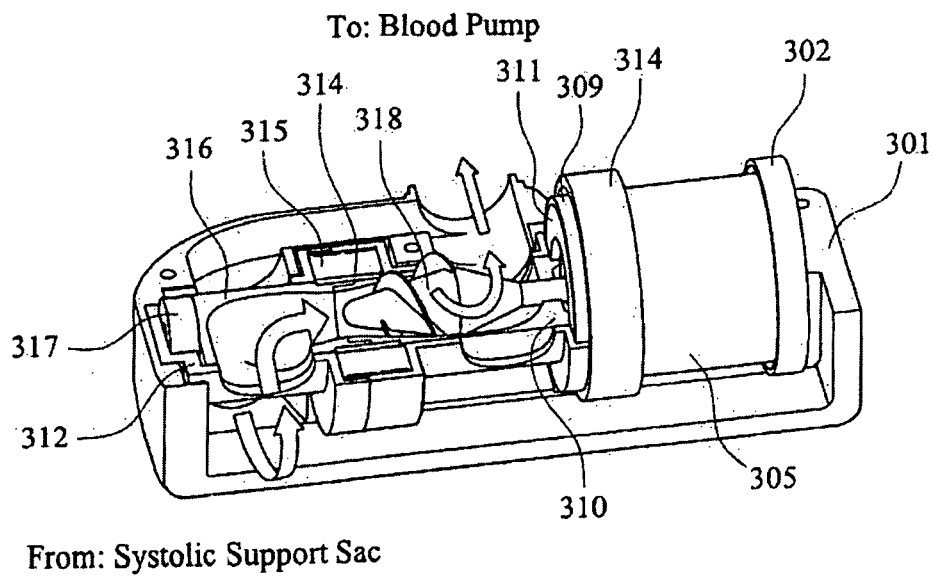
FIG. 9b shows a flow passage in the mixed-flow electro-hydraulic driver in FIGS. 8a and 8b, wherein the flow passage is from sac to blood pump.

A DC brushless torque motor, formed by the motor casing 305, the motor stator 306, and the motor rotor 307, drives this mixed-flow impeller 318 with a typical speed range of 5,000-12,000 rounds per minute (RPM). Around 11,000 RPM, at least 20 liter/min (LPM) flow rate should be delivered against 120 mmHg pressure rise at the aortic site. The impeller was designed and optimized by using computational fluid dynamics (CFD) analysis. A stepping motor, formed by the motor rotor 314 and the motor stator 315, is installed around the waist of the switching valve (313, 316). This stepping motor (314, 315) can align together the inflow/outflow aperture pairs which are drilled respectively on the side walls of the stationary casing (310, 312) and the inner rotating switching valve (313, 316). The stepping motion is regulated by a controller using ECG waveform as the reference for developing counter-pulsation pumping. Both motors revolve uni-directionally so as to minimize the energy consumption due to direction reverse. Two flow passage routes, as determined by the switching valve motion, will direct the pressurized oil flowing back and forth between the blood pump and the sac via an inflow/outflow port 320 and an outflow/inflow port 319 formed on the driver casing 301. As shown in FIGS. 2b and 2c, the blood pump 200 is connected to the driver 300 via a cannula 321, and the sac 500 is connected to the driver 300 via another cannula 322. This integrated driver and flow passage system is shown in FIG. 9a and FIG. 9b. Note that all electric and mechanical components are immersed in the oil chamber. Excellent cooling and lubrication can be achieved to maintain the long-term patency of this EH driver.

Centrifugal Driver

Figure 10A:
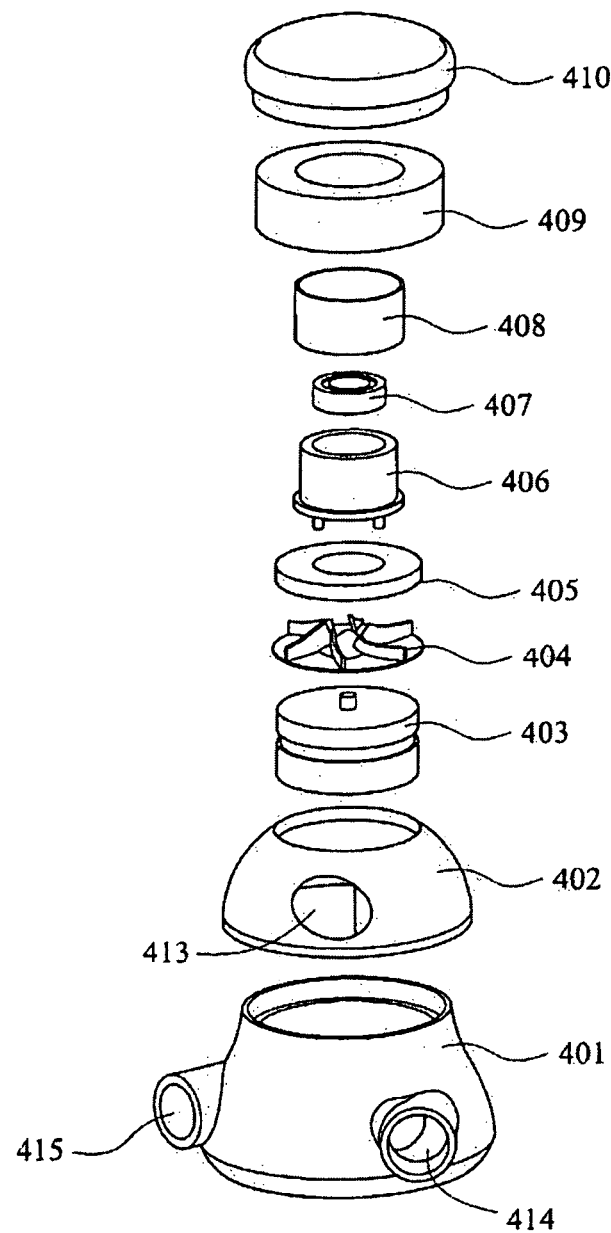
FIG. 10a is a perspective view of a centrifugal electro-hydraulic driver used in the present invention before assembly.
Figure 10B:
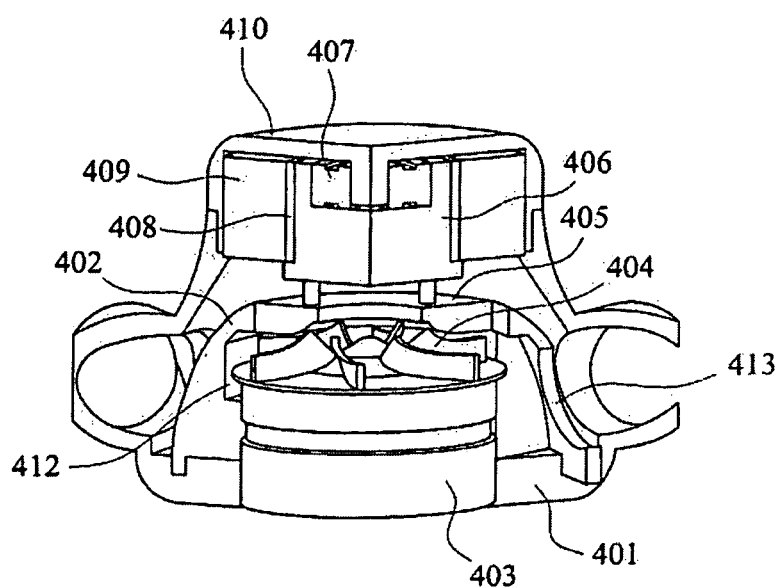
FIG. 10b is a partial cross-sectional view of the centrifugal electro-hydraulic driver in FIG. 10a after assembly.

An electro-hydraulic driver using a centrifugal impeller for pumping silicon oil constructed according to one of the preferred embodiments of the present invention is shown in FIGS. 10a and 10b, which is assembled with the flowing elements/parts:

401 Driver Casing,
402 Dome Valve,
403 Torque Motor,
404 Centrifugal Impeller,
405 Dome Valve Head,
406 Switching Connector,
407 Bearing,
408 Stepping Motor Rotor,
409 Stepping Motor Stator, and
410 Driver Head.

Figure 11A:
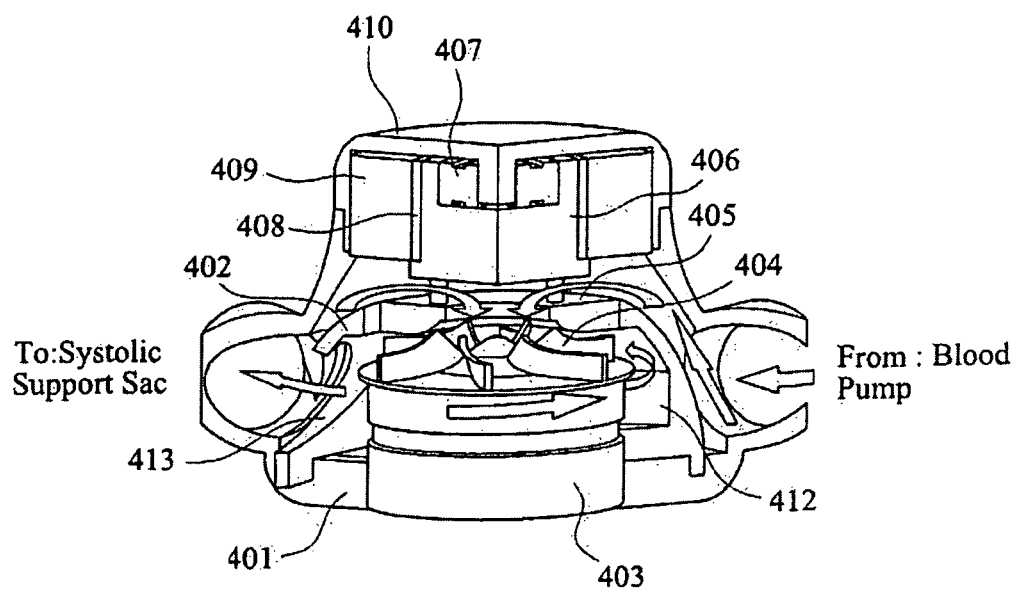
FIG. 11a shows a flow passage in the centrifugal electro-hydraulic driver in FIGS. 10a and 10b, wherein the flow passage is from blood pump to sac.
Figure 11B:
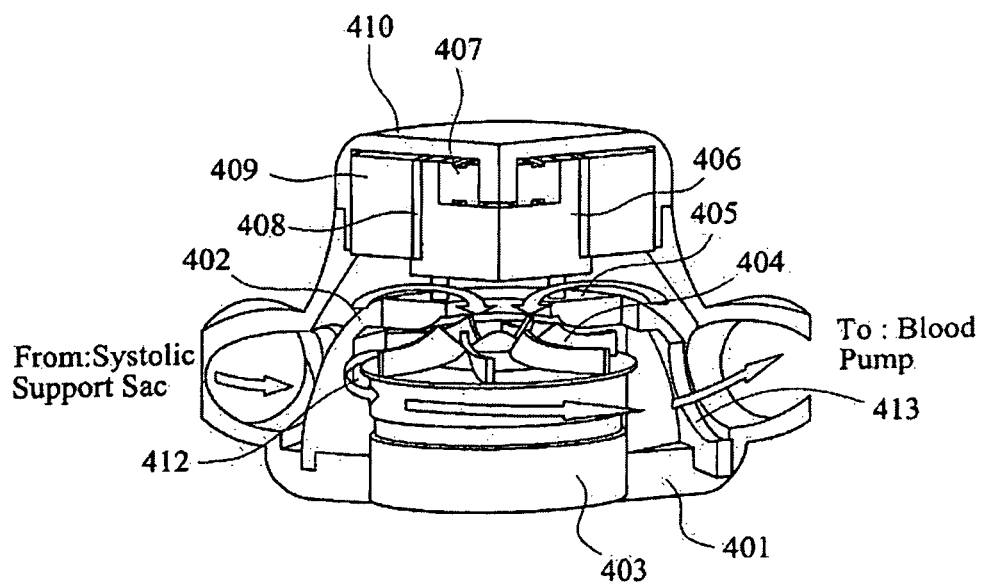
FIG. 11b shows a flow passage in the centrifugal electro-hydraulic driver in FIGS. 10a and 10b, wherein the flow passage is from sac to blood pump.

The flow passage which allows oil shuttling between sac and blood pump by this centrifugal driver is illustrated in FIGS. 11a and 11b. The impeller 404 was also designed using advanced CFD package assisted by an in-house design optimization procedure. The inlet and outlet diameters, of the radial impeller and the blade heights at inflow and outflow planes are appropriately chosen to attain a high pump efficiency spanning over a wide operational speed range. The design objective of the present centrifugal EH driver is set for delivering a volume flow rate (>20 LPM) against a pressure gradient of 200 mmHg at a rotational speed around 4000 to 8000 RPM. Metallic or ceramic ball bearing could be used for supporting the power transmission shaft which is also the rotor axis of the DC brushless torque motor 403. Both inner and outer spinning rotor designs can be used. Since silicon oil can purge the heat and debris generated within the bearing, a longer service life of the present EH driver can thus be guaranteed.

A bell-shaped switching valve, formed by the dome valve 402 and the dome valve head 405, regulates the flow and hydraulic power transmission directions. This bell-shaped switching valve is driven by a DC brushless stepping motor containing the stepping motor rotor 408 and the stepping motor stator 409. Windows are formed circumferentially around the upper end of the dome valve 402, and between the dome valve head 405 and the switching connector 406. The gap and recess created between the bell-shaped switching valve and the driver casing 401 of the EH driver forms an annular passage for the silicon oil flow to enter the impeller inlet. The inflow, coming either from the systolic sac or out of the blood pump, circulates around the annular gap, climbs up and enters through the opening windows of the dome and finally gets devoured into the impeller inlet eye.

The impeller-pressurized oil, however, is collected by a volute 412 whose outer wall is the dome valve 402. An aperture 413 is opened on the volute wall which, as rotates and aligns alternately with the two side cannulas connecting respectively to blood pump or systolic sac, fulfills the power deployment mission. A pair of "V-shaped" arms 414 and 415, which extrude respectively out from the left and right sides of the EH driver casing 401, forms the inflow/outflow tracts for shuttling the working fluids back and forth between the blood pump and the sac. EH driver can be viewed as a pressurization unit which alternately sloshes oil flow between its two ends, one being the low-pressure ventricular side (~0 mmHg) and the other the high-pressure (80-120 mmHg) aortic side. Preferred high-performance outflow tract angle is assigned to the volute while pumping the blood pump. Extra loss will be incurred during the subsequent withdrawal of oil flow back from the bipod pump due to the sharp turn of the outflow tract at the volute exit. However, this loss would be compensated by the higher preload condition of the aorta when shuttling oil back from the blood pump to compress the ventricles.

2. Extra-Corporeal Driver System

Extra-corporeal driver system can be either a bedside of a portable unit. The bedside model is used primarily in the intensive care unit (ICU) in a hospital. The portable model, however, is designed for outpatients when discharged after the DPbi-VAD implantation and being cleared from the post operational care period.

Extra-corporeal driver systems could be propelled by either pneumatic or hybrid pneumatic/electro-hydraulic power source, as described below. In order to minimize the infection possibility caused by the percutaneous drive, lines, thin pneumatic lines like those used by IABP are adopted. Basically, for all the extra-corporeal systems described below, the intra-thoracic fluid power actuation lines that connect respectively with the implants, i.e. the blood pump, and the sac, are thin pneumatic tubes in which inert, low molecular weight gas such as helium is running. At the outlet of each intra-thoracic pneumatic drive line, a dermal button is implanted under the skin, allowing convenient quick attachment/disconnection of the inner pneumatic drive line to the outside power source system.

For all the extra-corporeal drivers the intra-thoracic power transmission design is the same. By plugging on/off the exterior drive lines which connect either to the bedside console or to the portable DPbi-VAD driver unit, the patients implanted with the present intrathoracic device may be either bedridden or ambulant depending on the medical treatment and the life style the patients are having.

2.1 Bedside Driver System

Because the present DPbi-VAD uses the same operational principles as does the IABP, the IABP driver consoles can be employed as the driver system for pumping DPbi-VADs. Adaptor can be designed to connect DPbi-VAD to the IABP consoles, with pneumatic volume and pumping pressure adjusted according to the DPbi-VAD operational requirements. In general, two IABP drivers with asynchronous actuations of blood pump and sac are required for driving a DPbi-VAD system. Separate application of counter-pulsation and co-pulsation can also be selected for patients who require only one circulation support modality under certain clinical conditions.

Another embodiment of the bedside, DPbi-VAD is accomplished using; a designative driver system. This bedside driver is almost an identical equipment derived from the portable DPbi-VAD driver as illustrated below. The only differences lie in first, the electric power supply module allows for receiving the wall alternative electric current aside from the battery-supplied direct current; and, second, a more, sophisticated monitoring/display/adjustment system is equipped for the medical personnel to reference and control.

2.2 Portable Driver System

Figure 12:
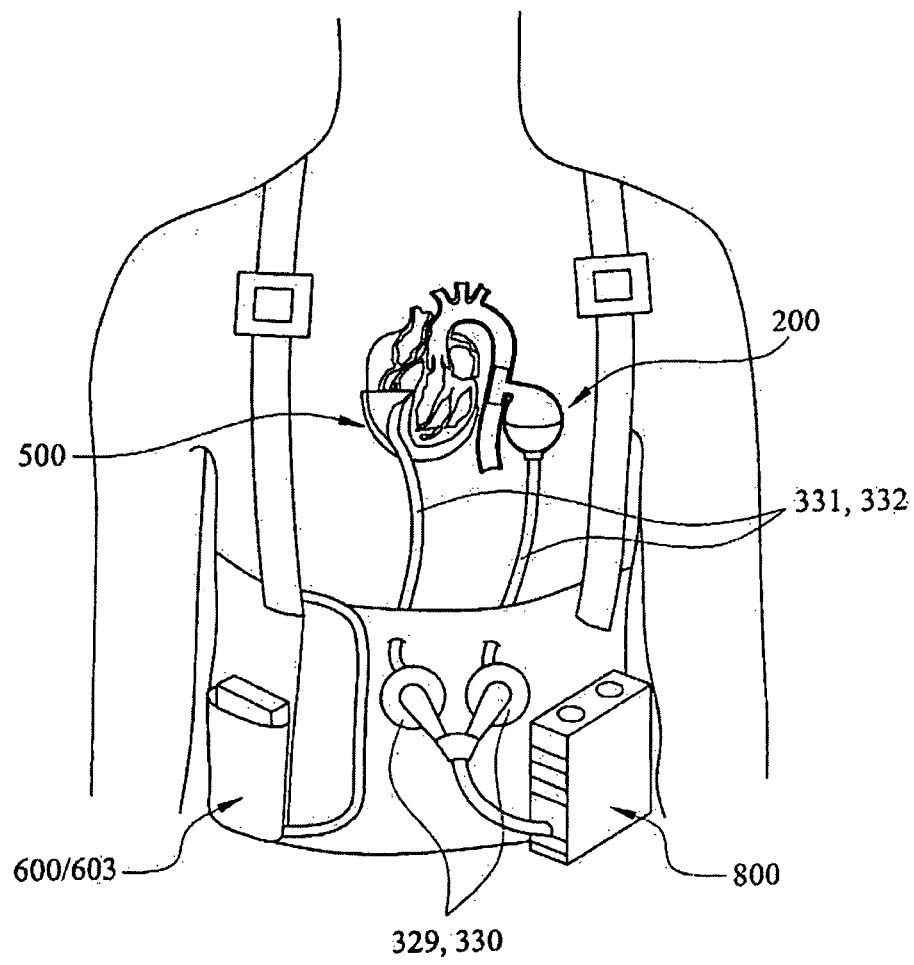
FIG. 12 is a schematic view showing a portable DPbi-VAD system layout of the present invention.
Figure 13:
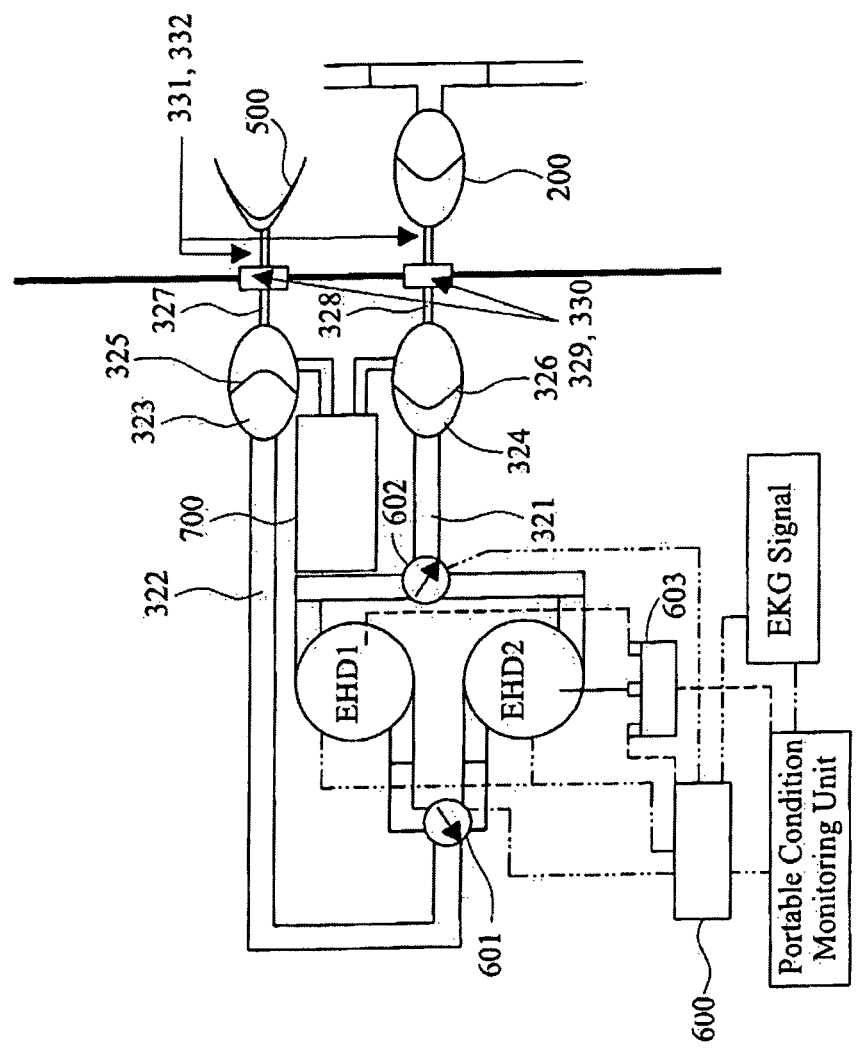
FIG. 13 is a schematic diagram showing details of the portable DPbi-VAD system in FIG. 12.

Portable driver is designed for patients who are cleared from the ICU stage. The present portable system is a variant of the intra-corporeal driver described previously. FIGS. 12 and 13 illustrate the idea of how this hybrid pneumatic/electro-hydraulic driver system is constructed. This system, in fact, is derived from the infra-corporeal EH driver by relaxing the space/anatomic constraint. The impeller size and the rotational speed of the torque motor can be modified to account for losses incurred in the longer fluid pathways associated with the extra-corporeal system. The volute inflow/outflow tracts are aligned tangentially to the volute body so sharp turn in the fluid pathway is eliminated to achieve a better hydraulic efficiency. Connected to the inflow/outflow cannulas 321 and 322 of are now two reservoirs 323 and 324 instead of the original blood pump 200 and sac 500 that were designed for the intra-corporeal system. Each reservoir is divided by layers of elastic membranes 325 and 326 into two partitions filled by silicon oil and helium gas, respectively. At the proximal helium partition side of each reservoir a pneumatic line 327 (328) exits and connects to the intra-thoracic unit via a specially designed anti-infection skin button 329 (330). When operated, the impeller-driven shuttling silicon oil will create compression and vacuum power onto the two neighboring reservoirs 323 and 324, hence driving the helium air and resulting in a simultaneous actuation of the bipod pump 200 and the sac 500 implanted in the patient's thoracic chest.

Multiple-redundancy can be enforced using multiple hybrid drivers. Double-redundancy using two driver units EDH1 and EDH2 arranged in parallel is exemplified in FIG. 13. As pump malfunction is detected, the electronic controller 600 will immediately send out a command signal to start the spared driver and a non-stopping, continuous driving motion can thus be guaranteed. Control valves 601, 602 are installed in the junctures of the fluid pathways to regulate the actuated fluid direction. An alternative, intermittent operation of the two EH drivers can also be designed using control logic programmed in the controller. By interchangeably providing appropriate idle time to each EH driver, an overall prolonged service life of the portable driver system can be attained.

Each reservoir 323 (324) has a pneumatic line connected to the helium replenishment system 700. Appropriate helium volume can be selected for treating different heart failure syndromes encountered clinically. The replenishment procedure is similar to those being implemented with the IABP systems. After reconnection of the extra-corporeal pneumatic lines 327 and 328 and infra-corporeal pneumatic lines 331 and 332, helium volume has to be completely drained first and then replenished to the required volume.

Comparing to the contemporary pneumatic driver systems which use bulky and heavy reciprocal engine and storage tanks, the present turbomachinery system is much light-weighted and quieter. Subsystems such as battery pack 603, electronic controller 600, and the hybrid pneumatic/electro-hydraulic units 800 are integrated into boxed canisters, which could easily be carried by a patient using wearable jacket, as depicted in FIG. 12. It has always been welcome to have a VAD system with minimal modules that have to be implanted inside the human body. For the present portable DPbi-VAD, the complex electro-mechanical and power supply/control modules are all placed extra-corporeally. Not only regular inspection and maintenance of the driver and controller can be allowed, the heat generated by the driver during operation can also be dumped easily to the atmosphere. In case of emergent machine malfunction, a quick replacement of the faulty unit can also be carried out. Great mobility and safety operation is hence guaranteed by this portable driver system. Since the pulsatile operation of blood pump and sac is non-obligatory, stoppage of the DPbi-VAD is allowable for a certain period of time (a few minutes to a fraction of hour per se). This will further provide convenience and freedom for patients to put on/off the DPbi-VAD jacket for routine events, such as changing clothes and/of taking bath that are frequently happening in a real life.

d. Physiological Controller

The objective of the present controller design aims at developing a scheduled timing and forcing level control for the EH driver. A successful enforcement of systolic unloading, diastolic augmentation and epicardial compression calls for a delicate phase manipulation in relation to the heart rhythm. Systolic unloading and epicardial compression are enforced as a pair of a single actuation and the initiation is best set at the time when the ventricles are just about to contract. Diastolic augmentation, however, is initiated during heart diastole when the aortic valve is just closed (starting from the dicrotic notch of the aortic pressure; trace) and the coronary arterial walls begin to relax. All these actuation controls need to use ECG or aortic pressure waveform as a base of reference. Suppose that ECG signal is adopted for pumping control, algorithm has to be developed to recognize the R-wave out of other wave characteristics on the ECG signal trace. Similar waveform recognition method can readily be developed if aortic pressure is selected as the sensor signal.

Cardiac output can be taken as a product of stroke volume multiplied by heart rate. Physiological heart regulation is realized by adjusting stroke volume and heart rate autonomously via nervous and hormonal control. Usually higher heart rate corresponds to larger heart muscle contractility and hence elevated stroke volume. Therefore, a physiological controller that mimics the natural cardiac regulation can be built based on heart rate alone, leaving ECG signal the only required control input. Since R-wave is tracked, the pumping frequency of the EH driver can be determined, which may be identical, or in proportional to the detected heart rate. This characteristic makes the present device operate in response to the physiological circulation need. It should be noted that as much frequent electro-hydraulic pumping ejection is fulfilled by a faster switching valve aperture crossing, the cross-flow resistance of the aperture will increase accordingly. The impeller-delivered hydraulic pressure should therefore be elevated to overcome the aperture loss and the higher ejection inertia required. The speed control of the stepping and torque motors should therefore be coordinated using appropriate control logic, resulting in a situation that circulation assistance is physiologically enforced to meet the cardiac output requirement and the therapeutic purposes as well. In case of arrhythmia, a default pumping scenario of fixed pumping frequency will dictate irrespective of the arrhythmic ECG signal.

The actuator system of the present controller consists of two motors, driving respectively the switching (or dome) valve for frequency or heart rate control and the impeller for mechanical power delivery regulation. Because mixed-flow and centrifugal EH drivers are similar in the sense of controller development, we shall illustrate in the following the control design of the centrifugal pump only. Equivalent control design for mixed-flow pump can be achieved by a minor adjustment of the parameters involved.

Figure 14:
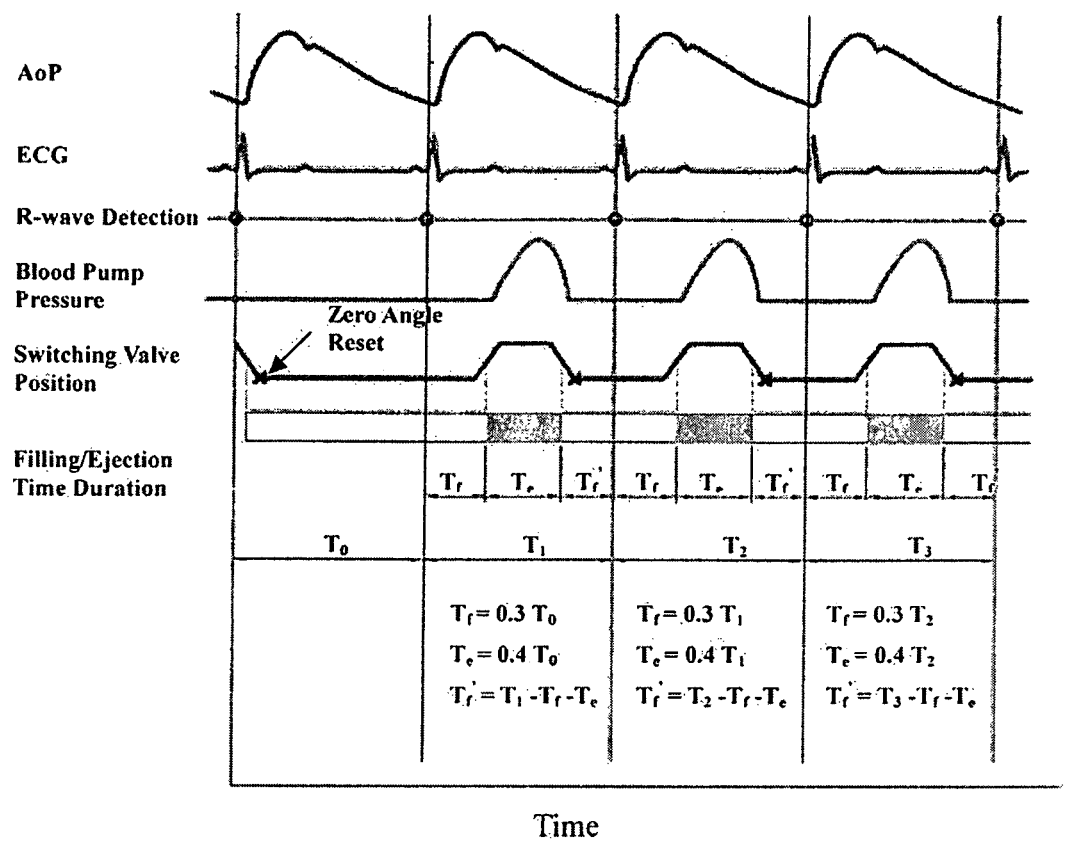
FIG. 14 is a plot showing dual-pulsation control schedule, wherein AoP aortic pressure, ECG: electrocardiogram, $T_0$, $T_1$, $T_2$, $T_3$: consecutive periods, $T_f$, $T_f$: blood pump filling durations, and $T_e$: bipod pump ejection duration.
Figure 15:
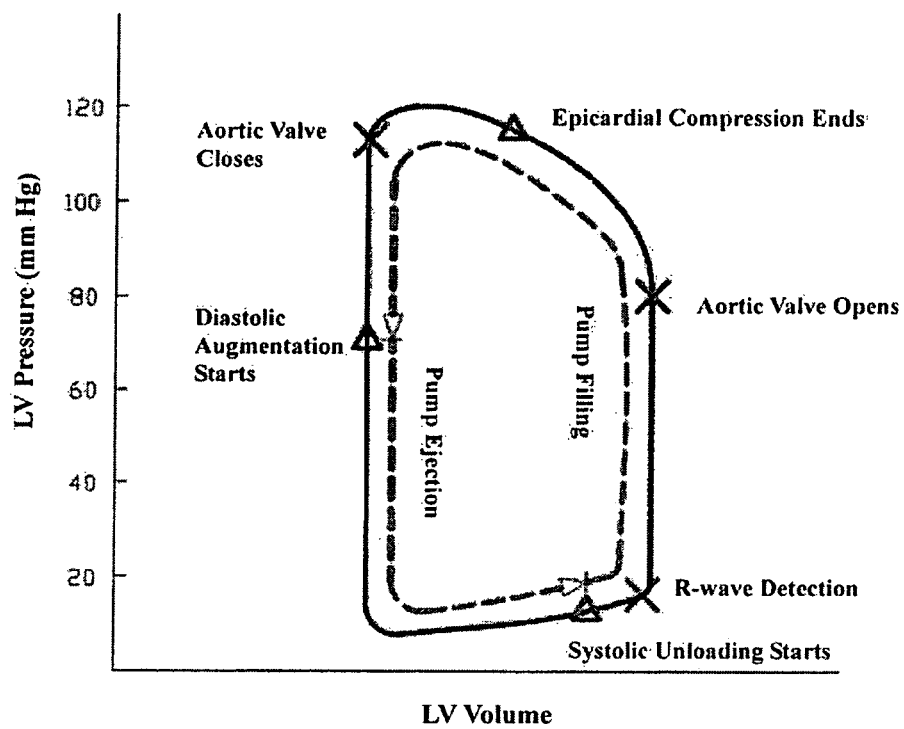
FIG. 15 is a plot showing the left ventricular (LV) pressure-volume relationship vs. dual-pulsation pumping operation.

For the centrifugal EH driver, a stepping motor is mounted onto the dome valve head for position and motion control. In controlling the oil flow directions the stepping motor revolves continuously or intermittently and uni-directionally. In each heart beat the pumping control can be divided into two phases. The first is the systolic unloading control in the aortic side and, spontaneously, the epicardiac compression in the ventricular side. The second is the diastolic augmentation control while the sac functions like a slaved oil pouch. For both systolic and diastolic actuations, each pumping control basically consists of three steps, starting with the initiation control and then followed by a position and a duration control. The initiation control decides when the control action commences. The position control drives the dome aperture to align with the inflow/outflow ports. The duration control, however, determines how long/the pump ejection should last upon the completion of the aperture alignment. All these six control steps are accomplished in one heart beat cycle using the prior detected time period as a base for defining the control algorithm. FIG. 14 illustrates the control schedule in conjunction with the hemodynamics, valve motion and cardiogram in consecutive cardiac cycles. These timing and period of control actuations are further translated into the pressure-volume relationship of the left ventricle, as shown in FIG. 15.

On FIG. 14 there are four consecutive heart cycles that are shown to illustrate the present control algorithm. The default position is the position where impeller volute aperture aligns with the inflow port/cannula leading to the sac. This is also the position the reference zero-degree angle is defined and reset after each revolution. At cycle $0$ the control is yet initiated and the switching valve is located at the default zero-degree position. The driver sits still with pumping direction oriented for systolic unloading. As two consecutive R-waves are detected, the cycle period $T_0$ is calculated and two time intervals $T_f$ and $T_e$, which are proportional to $T_0$, are determined accordingly. A pair of parameters, which define the proportions of $T_f$ and $T_e$ relative to the available cycle period $T_0$, is preset initially in the control logic. Diastolic augmentation commences at the end of the first elapsed time interval $T_f$. At this instant, position control would quickly move and align the dome valve aperture with the outflow port/cannula to the blood pump. Diastolic augmentation is then enforced until the $T_e$ interval is ended. Upon completion of diastolic augmentation, the stepping motor is actuated to continue the rotation and reposition the valve aperture in alignment with the inflow port/cannula to the sac. Systolic unloading is immediately activated upon the completion of aperture alignment. Roughly speaking, a residual time duration will take up the remaining pumping cycle before the next R-wave onset. This means that, the aortic pressure has already been declined prior to the heart systole. When new R-wave is detected, an updated cycle period $T_1$ becomes available and the following two time intervals $T_f$ and $T_e$ are re-calculated. This cyclic control command sequence will recursively be created and executed with new R-waves being consecutively detected.

A photo detector sensor pair is mounted on the dome valve and the driver casing to help reposition the default position of the dome valve as one 360-degree revolution is completed in a cycle. The zero-degree reference position is redefined in each cycle as the photo detector pair aligned together. In the present design the zero-angle position is set where the apertures are aligned to enforce systolic unloading. This reposition control can prevent accumulated angular drift and assures in each beat the volute aperture would align correctly with the Outflow tract.

Owing to the fact that larger through-flow aperture corresponds to lower ejection loss, the control logic should be selected, under the power limit of the stepping motor, to maximize as fast as possible the rotational acceleration for positioning the dome valve aperture in alignment with the right or left outflow tracts. Systole/diastole ratio can be adjusted to yield an optimal diastolic augmentation and the assistance to the systemic circulation as well. In situation of arrhythmia, or heart rate larger than certain limit (i.e. 100 beats per minute), the controller will ignore the cardiogram and gives either a fixed rate or a reduced 1-to-2 or 1-to-3 pulsation command to yield an optimal cardiac support, same as those supplied by the IABP control logic.

A DC brushless torque motor provides the main driving force for the impeller. The power is supplied by a battery pack and regulated by a speed controller. This torque motor is expected to deliver a power output ranging from 20 to 30 watts. As heart rate increases, the aperture resistance and the arterial pressure both elevate, requiring a larger pumping force to achieve the desired cardiac output requirement. Either passive or active torque motor control can be adopted to cope with this physiological demand. A predetermined piece-wise RPM target schedule, for example, can be set for a heart beat range for the passive control with an autonomous RPM tracking control being implemented in the motor drive. Sophisticated active physiological control can also be considered, which calls for more sensors or information be supplied to reflect the demand of the body or the regulation rule the cardiac function is supposed to possess.

e. Sac

Integration of bi-ventricular systolic compression with counter-pulsation circulation assist is a unique feature of the present invention. Originally, for pulsatile LVAD devices, the heed of a compliance chamber has been a necessary liability because pulsation requires additional volume to undergo the back-and-forth displacement of the stroke volume. Hence, the space required for device implantation is doubled. The implementation of sac turns this disadvantage into advantage. When sac inflates, the ventricles contract, and vice versa when sac deflates. The space for accommodating this sac, therefore, does not occupy too much additional space since it dynamically shares the space with the natural ventricles.

According to the preferred embodiments the present sac consists of two sheets of polyurethane (PU) foils. One, the outer shell, which is semi-rigid but non-distensible, or is substantially rigid, is embedded with textile nets to restrain its stretching deformation. The other, being an elastic diaphragm used to assist heart contraction, is a thin flexing membrane made by solution dip method. The size and morphology of these two PU foils are, in principle, chosen to be almost identical to those of the heart in the end-of-diastolic condition. For dilated failing hearts, appropriate sizing of the sac can be employed to limit further pathological dilatation. Clinically it was observed that heart with pathological dilatation may have very irregular shape. To achieve an effective epicardial compression, the fitness of sac in regard to the diseased heart shape is very important. Customized sac can be fabricated using the CT-scanned images taken prior to the implantation.

Figure 16A:
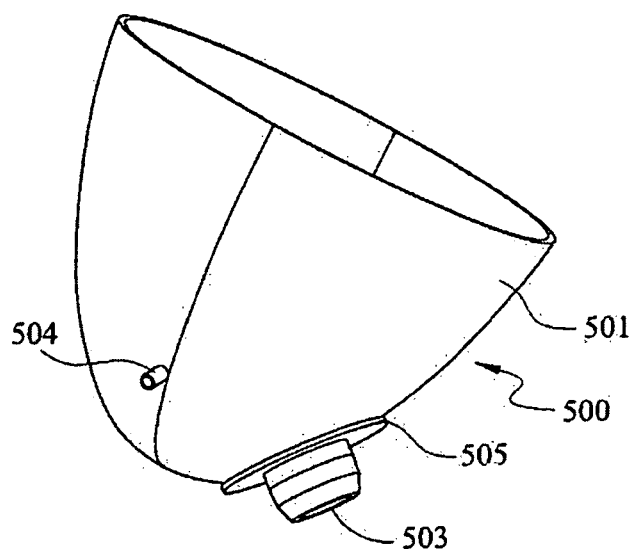
FIG. 16a is a schematic perspective view showing a sac of the present invention.
Figure 16B:
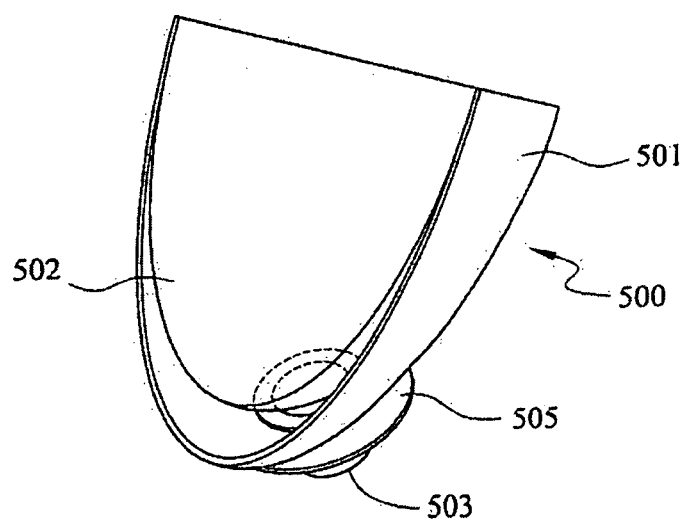
FIG. 16b is a schematic perspective view showing the sac in FIG. 16a with a portion thereof being cut off.

Depicted in FIGS. 16a and 16b is a schematic of the present sac 500. The outer shell 501 and the elastic membrane 502 are fused together around the sac rim by the PU solvent or other methods to result in a sealed volume closure. In other words, the elastic membrane 502 hermetically attached to the inner surface of the outer shell 501. Moreover, the combination of the outer shell 501 and the elastic membrane 502 form one or more inflatable chambers: A conduit 503 is provided on the non-flexing outer shell 501, which allows silicon oil be injected into and/or withdrawn from the sac 500. A opening for de-airing 504 is installed on the outer shell to help facilitate air removal whenever deemed necessary. In general, each inflatable chamber has one opening for de-airing. It is worthy noticing that the elastic membrane 502 has no attachment spots with the outer shell except the peripheral rim. This free-movement characteristic of the elastic membrane provides the sac a greater ability in shape adaptation. Moreover, the present elastic membrane design is particularly meaningful in minimizing the relative movement occurring between the elastic membrane and the heart skin. Myocardial contusion or scar tissue formation can thus be greatly avoided. Further, each of the inflatable chambers could be controllably connected to a driver, wherein the inflation of the inflatable chambers is individually adjustable.

In the installation of the sac, the pericardium is first dissected and the fluid drained to allow the insertion of the sac. Sac is then inserted through the pericardial opening to allow a snug wrapping of the sac around the heart. Note that the sac should only wrap around the right and left ventricles. This sizing control can prevent the delivered hydraulic pressure from compressing the atria. This consideration is essential for maintaining a reasonable and low end-diastolic-pressure, avoiding the impairment of the subsequent filling of the ventricles. Sometimes, compressing atria during ventricle systole might cause premature opening of the atrio-ventricular valves, which is particularly undesirable for patients with incompetent valves. In all, care must be exercised in contouring the sac configuration, making atria cleared out from the wrapping of the sac. Isolation of atria from systolic compression support is necessary; otherwise, the venous return and pulmonary vein pressures will be elevated due to the applied compression force.

The thin PU sheets in contact with the ventricles are very compliant and shape conformal. The remaining myocardial fluid on the heart skin works as a liquid film to help compel out the air trapped; initially when sac is mounted on the ventricles. It was found in the in-vivo experiments that typically a few pumping strokes will squeeze: out air bubbles initially trapped, making the inner membrane of the sac firmly attached on the ventricle skin. Coronary perfusion would not be significantly impaired because the sac works synchronously with the heart. In diastole, both heart and sac are relaxed, which encourages coronary perfusion. Since the sac membrane is firmly attached on the heart skin, during diastolic augmentation stroke the vacuum created in the sac may generate a suction effect on the ventricle free wall, which is beneficial for increasing the end-of-diastolic volume and Hence the stroke volume. In addition, this suction effect helps to expand the coronary arterial lumen also, creating another salutary effect in enhancing the coronary flow.

Fixation of sac holds an important role on upholding the performance of direct cardiac compression. As ventricle systoles, the resultant reaction force exerting on the sac points approximately in the apical direction in the septum plane. This reactant force is mainly resisted by the oil conduit strut which is supported in turn by the implanted EH driver. A cuff ring 505 is made around the conduit 503 located at the base of the sac 500. This base cuff ring 505 can be tightly sutured onto the epicardium to help control the orientation and fixation of the sac. If necessary, additional fixation can be made by sewing or anchoring other sac cuffs (not shown in the figures) onto the surrounding pleural tissues and/or bone structures.

Bi-ventricular circulation support is provided by the sac since both left and right ventricles are wrapped in. In the systolic unloading mode, a volume of silicon oil no greater than the cardiac stroke volume will be sloshed into the sac. This shuttled volume, typically 30~90 c.c., will be redistributed in the inward volume recess created by the contraction of both left and right hearts. Note that this shuttled volume occupies only a portion of the total stroke volume contributed by the left and right heart contraction. The effective epicardial compression action, therefore, only takes place in the initial compression phase. In other words, the ventricles are boosted in the foremast part starting from, or just before, isovolumetric contraction to the early stage of blood ejection. For the rest contraction period, the sac will be passively carried by and moved inward together with the contracting heart muscle. This limited inward power stroke of the sac can prevent the right heart from being overtly compressed. Nevertheless, direct contact of the heart muscle by the sac still effectively helps the initial muscular shortening which is known to be crucial in reducing the myocardial oxygen consumption.

In summary, the functions of the sac are multitude. First, it works as an artificial pericardial pouch which protects the heart from contusion and absorbs the vibration or impact momentum exerted from outside. Second, in diastole, it plays the role of restraining heart from further abnormal dilation. Third, and most importantly, it assists both right and left heart contractions to result in a balanced circulation support, avoiding the frequently observed LVAD-induced complication of right heart failure due to left heart support. Direct sac compression can increase the contractility of the diseased ventricles and, as incorporated with counter-pulsation circulation assist, not only help fill the blood pump but also prevent excessive unloading which is known to be detrimental to coronary perfusion augmentation.

f. Energy/Information Transfer System

Both percutaneous and transcutaneous energy/information transfer systems can be considered. For percutaneous system, the implanted components are lesser, which eases the surgical operation at the price of increasing the possibility of post-operational infection. Electrical energy and sensor/commanding signal transfer is more reliable and efficient as hard wires are used. Interferences caused by wireless energy/data transmission can be minimized. Besides, the infra-thoracic heat release will also be reduced because many heat generating electronic equipments, such as motor controllers, battery, and data acquisition and processing units, are not intra-corporeally implanted.

Transcutaneous transfer system is welcome because it provides the highest quality of life for the patients. Because extra components, such as internal charge battery set and electronic controllers must be implanted, the bulkiness of the implantable VAD system increases. In order to transfer the internally produced heat out from the implants, the heat generating components had better be packaged in the EH driver, which will enlarge the EH driver volume size accordingly.

The features as described above which are not claimed in the pending claims would be claimed in divisional applications of the present application.

What is claimed is:

1. A manifold for accessing blood from a human blood vessel, the manifold comprising a first and a second pathway intersecting with each other at an angle, the first pathway being configured and adapted to be completely embedded in the human blood vessel with the second pathway extending external the human blood vessel wherein the manifold is configured to be substantially retained by the human blood vessel through engagement of an outer surface of said first pathway with an inner surface of said human blood vessel throughout an entire length of said first pathway and devoid of any other artificial interior coupling of said manifold to said human blood vessel, said first pathway having an outer wall diameter equal to or larger than an inner wall diameter of the blood vessel and captured in the blood vessel by the extension of the second pathway through an opening in a sidewall of the blood vessel, thereby maintaining the manifold in a stable, constrained position within the blood vessel.

2. The manifold of claim 1, wherein the manifold is made of a biocompatible material selected from the group consisting of metal and elastic polymer.

3. The manifold of claim 1, wherein the wall thickness of the manifold gradually decreases toward a first and a second end of the first pathway.

4. The manifold of claim 1, wherein the wall of the manifold is perforated along the first pathway.

5. The manifold of claim 1, wherein the wall of the manifold is textured along the first pathway.

6. The manifold of claim 1, wherein the diameter of the outer surface of the first pathway of the manifold is configured to be approximately 5%-20% larger than the diameter of the inner surface of the human blood vessel.

7. A manifold for accessing blood from a human blood vessel, the manifold comprising a first and a second pathway intersecting with each other at an angle, the first pathway being configured and adapted to be completely embedded in the human blood vessel with the second pathway extending external the human blood vessel wherein a diameter of an outer surface of the first pathway of the manifold is configured to be approximately 5%-20% larger than a diameter of an inner surface of the human blood vessel and the manifold is configured to be substantially retained by the human blood vessel through engagement of the outer surface of said first pathway with the internal surface of said human blood vessel throughout an entire length of said first pathway and devoid of any other artificial interior coupling of said manifold to said human blood vessel, said first pathway is captured in the blood vessel by the extension of the second pathway through an opening in a sidewall of the blood vessel, thereby maintaining the manifold in a stable, constrained position within the blood vessel.

8. The manifold of claim 7, wherein the manifold is made of a biocompatible material selected from the group consisting of metal and elastic polymer.

9. The manifold of claim 7, wherein the wall thickness of the manifold gradually decreases toward a first and a second end of the first pathway.

10. The manifold of claim 7, wherein the wall of the manifold is perforated along the first pathway.

11. The manifold of claim 7, wherein the wall of the manifold is textured along the first pathway.

12. A manifold for accessing blood from a human blood vessel, the manifold comprising a first and a second pathway intersecting with each other at an angle, both the first and second pathways having a circular cross-section, and the first pathway being configured and adapted to be completely embedded in the human blood vessel with the second pathway extending external the human blood vessel wherein the manifold is configured to be substantially retained by the human blood vessel through engagement of an outer surface of said first pathway with an inner surface of said human blood vessel throughout an entire length of said first pathway and devoid of any other artificial interior coupling of said manifold to said human blood vessel, said first pathway having an outer wall diameter equal to or larger than an inner wall diameter of the blood vessel and captured in the blood vessel by the extension of the second pathway through an opening in a sidewall of the blood vessel, thereby maintaining the manifold in a stable, constrained position within the blood vessel.

13. The manifold of claim 12, wherein the manifold is made of a biocompatible material selected from the group consisting of metal and elastic polymer.

14. The manifold of claim 12, wherein the wall thickness of the manifold gradually decreases toward a first and a second end of the first pathway.

15. The manifold of claim 12, wherein the wall of the manifold is perforated along the first pathway.

16. The manifold of claim 12, wherein the wall of the manifold is textured along the first pathway.

17. A manifold for accessing blood from a human blood vessel, the manifold comprising a first and a second pathway intersecting with each other at an angle, the first pathway having a circular cross-section and being configured and adapted to be completely embedded in the human blood vessel with the second pathway extending external the human blood vessel wherein the manifold is configured to be substantially retained by the human blood vessel through engagement of an outer surface of said first pathway with an inner surface of said human blood vessel throughout an entire length of said first pathway and devoid of any other artificial coupling of said manifold to said human blood vessel, said first pathway having an outer wall diameter equal to or larger than an inner wall diameter of the blood vessel and captured in the blood vessel by the extension of the second pathway through an opening in a sidewall of the blood vessel, thereby maintaining the manifold in a stable, constrained position within the blood vessel.

* * * * *